US010969316B2

(12) United States Patent
Bai et al.

(10) Patent No.: US 10,969,316 B2
(45) Date of Patent: Apr. 6, 2021

(54) QUANTITATIVE IN-SITU TEXTURE MEASUREMENT APPARATUS AND METHOD

(71) Applicant: Frito-Lay North America, Inc., Plano, TX (US)

(72) Inventors: Ou Bai, Plano, TX (US); Wilfred Marcellien Bourg, Jr., Melissa, TX (US); Enrique Michel-Sanchez, Dallas, TX (US); Shahmeer Ali Mirza, Dallas, TX (US)

(73) Assignee: Frito-Lay North America, Inc., Plano, TX (US)

( * ) Notice: Subject to any disclaimer, the term of this patent is extended or adjusted under 35 U.S.C. 154(b) by 873 days.

(21) Appl. No.: 15/448,853

(22) Filed: Mar. 3, 2017

(65) Prior Publication Data

US 2017/0176309 A1 Jun. 22, 2017

Related U.S. Application Data

(63) Continuation-in-part of application No. 15/380,622, filed on Dec. 15, 2016, now Pat. No. 10,048,232, (Continued)

(51) Int. Cl.

*G01N 33/02* (2006.01)
*G01N 3/32* (2006.01)

(Continued)

(52) U.S. Cl.

CPC ................ *G01N 3/32* (2013.01); *A23L 33/10* (2016.08); *G01N 29/11* (2013.01); *G01N 29/12* (2013.01);

(Continued)

(58) Field of Classification Search

CPC ...... G01N 33/02; G01N 33/025; G01N 33/03; G01N 33/04; G01N 33/06; G01N 33/08;

(Continued)

(56) References Cited

U.S. PATENT DOCUMENTS

| | | | |
|---|---|---|---|
| 4,051,372 | A | 9/1977 | Aine |
| 4,169,662 | A | 10/1979 | Kaule et al. |

(Continued)

FOREIGN PATENT DOCUMENTS

| | | |
|---|---|---|
| DE | 329319 | 11/1920 |
| DE | 3939411 | 6/1991 |

(Continued)

OTHER PUBLICATIONS

Srisawas et al. "Acoustic Testing of Snack Food Crispness Using Neural Networks" Journal of Texture Studes, vol. 34 (2003) pp. 401-420.

(Continued)

*Primary Examiner* — Lisa M Caputo
*Assistant Examiner* — Alex T Devito
(74) *Attorney, Agent, or Firm* — Barnes & Thornburg LLP; G. Peter Nichols

(57) ABSTRACT

A measurement apparatus and method for in-situ quantitative texture measurement of a food snack. The apparatus includes an acoustic capturing device and a data processing unit. The physical interaction in the mouth with saliva, when a human being eats/drinks a food snack, sends pressure waves that propagate through the ear bone and produce an acoustic signal. The acoustic capturing device records and forwards the signal to a data processing unit. The data processing unit further comprises a digital signal processing module that smoothens, transforms and filters the received acoustic signal. A statistical processing module further filters the acoustic signal from the data processing unit and gen- (Continued)

erates a quantitative acoustic model for texture attributes such as hardness and fracturability. The quantitative model is correlated with a qualitative texture measurement from a descriptive expert panel. Another method includes a food snack fingerprinting using an in-situ quantitative food property measurement.

14 Claims, 19 Drawing Sheets

Related U.S. Application Data which is a continuation of application No. 14/864,593, filed on Sep. 24, 2015, now Pat. No. 9,541,537, and a continuation-in-part of application No. 14/864,728, filed on Sep. 24, 2015, now Pat. No. 10,070,661.

(60) Provisional application No. 62/303,511, filed on Mar. 4, 2016.

(51) Int. Cl.

| | |
|---|---|
| ***G01N 29/12*** | (2006.01) |
| ***A23L 33/10*** | (2016.01) |
| ***G01N 29/11*** | (2006.01) |
| ***G01N 29/24*** | (2006.01) |
| ***G01N 29/44*** | (2006.01) |
| *G01H 9/00* | (2006.01) |

(52) U.S. Cl.
CPC ..... *G01N 29/2418* (2013.01); *G01N 29/4472* (2013.01); *G01N 33/02* (2013.01); *G01H 9/008* (2013.01); *G01N 2291/014* (2013.01); *G01N 2291/015* (2013.01); *G01N 2291/0289* (2013.01); *G01N 2291/02466* (2013.01); *G01N 2291/02818* (2013.01); *G01N 2291/02827* (2013.01)

(58) Field of Classification Search
CPC .... G01N 33/085; G01N 33/10; G01N 33/105; G01N 33/12; G01N 33/14; G01N 33/143; G01N 33/146; G01N 3/32; G01N 29/12; G01N 2291/02818
See application file for complete search history.

(56) References Cited

U.S. PATENT DOCUMENTS

| | | | | |
|---|---|---|---|---|
| 4,184,768 | A | 1/1980 | Murphy | |
| 4,187,026 | A | 2/1980 | Schaffer | |
| 4,234,258 | A | 11/1980 | Frosch | |
| 4,236,827 | A | 12/1980 | Horiba | |
| 4,325,252 | A | 4/1982 | Miller | |
| 4,381,148 | A | 4/1983 | Ulrich et al. | |
| 4,479,265 | A | 10/1984 | Muscatell | |
| 4,562,736 | A | 1/1986 | Iwasaki | |
| 4,866,283 | A | 9/1989 | Hill | |
| 4,899,589 | A | 2/1990 | Thompson | |
| 5,048,340 | A | 9/1991 | Thompson | |
| 5,070,733 | A | 12/1991 | Nagata | |
| 5,121,426 | A | 6/1992 | Baumhauer | |
| 5,151,590 | A | 9/1992 | Takamoto et al. | |
| 5,152,401 | A | 10/1992 | Affeldt | |
| 5,226,076 | A | 7/1993 | Baumhauer | |
| 5,251,486 | A | 10/1993 | Thompson | |
| 5,286,313 | A | 2/1994 | Schultz | |
| 5,372,030 | A | 12/1994 | Prussia | |
| 5,526,689 | A | 6/1996 | Coulter | |
| 5,588,428 | A | 12/1996 | Smith | |
| 5,691,473 | A | 11/1997 | Peleg | |
| 5,751,416 | A | 5/1998 | Singh | |
| 5,780,724 | A | 7/1998 | Olender | |
| 5,804,727 | A | 9/1998 | Lu | |
| 5,825,898 | A | 10/1998 | Marash | |
| 5,827,974 | A | 10/1998 | Nussinovitch | |
| 5,847,825 | A | 12/1998 | Alexander | |
| 5,848,172 | A | 12/1998 | Allen | |
| 5,922,387 | A | 7/1999 | Parada | |
| 6,034,768 | A | 3/2000 | Fraser | |
| 6,057,927 | A | 5/2000 | Levesque et al. | |
| 6,122,389 | A | 9/2000 | Grosz | |
| 6,276,536 | B1 | 8/2001 | Terasaki et al. | |
| 6,311,558 | B1 | 11/2001 | Clark | |
| 6,385,558 | B1 | 5/2002 | Schlemm | |
| 6,407,811 | B1 | 6/2002 | Snyder | |
| 6,466,309 | B1 | 10/2002 | Kossakovski | |
| 6,494,098 | B1 | 12/2002 | Leybovich | |
| 6,531,707 | B1 | 3/2003 | Favreau | |
| 6,532,821 | B2 | 3/2003 | Lamouche | |
| 6,539,781 | B1 | 4/2003 | Crezee | |
| 6,628,404 | B1 | 9/2003 | Kelley | |
| 6,657,721 | B1 | 12/2003 | Palleschi | |
| 6,694,173 | B1 | 2/2004 | Bende | |
| 6,753,957 | B1 | 6/2004 | Graft | |
| 6,771,368 | B1 | 8/2004 | Chadwick | |
| 6,792,324 | B2 | 9/2004 | Trinkel | |
| 6,823,736 | B1 | 11/2004 | Brock | |
| 6,857,317 | B2 | 2/2005 | Sakurai | |
| 6,909,505 | B2 | 6/2005 | Lucas | |
| 6,944,204 | B2 | 9/2005 | Zhou | |
| 6,987,564 | B2 | 1/2006 | Gornushkin | |
| 7,092,807 | B2 | 8/2006 | Kumar | |
| 7,117,034 | B2 | 10/2006 | Kronberg | |
| 7,165,451 | B1 | 1/2007 | Brooks | |
| 7,195,731 | B2 | 3/2007 | Jones | |
| 7,595,463 | B2 | 9/2009 | Weick | |
| 7,692,788 | B2 | 4/2010 | Popp | |
| 7,802,477 | B2 | 9/2010 | Sakurai | |
| 7,860,277 | B2 | 12/2010 | Mulder | |
| 8,319,964 | B2 | 11/2012 | Hahn | |
| 8,368,289 | B2 | 2/2013 | Karabutov | |
| 8,567,250 | B2 | 10/2013 | Loeser | |
| 8,619,255 | B2 | 12/2013 | Gennadievich | |
| 8,659,753 | B1 | 2/2014 | Cabaio | |
| 8,638,956 | B2 | 4/2014 | Deng | |
| 8,891,073 | B2 | 11/2014 | Effenberger, Jr. | |
| 9,032,798 | B2 | 5/2015 | Sakakibara | |
| 9,068,926 | B2 | 6/2015 | Schade | |
| 9,159,126 | B2 | 10/2015 | Johnson | |
| 9,285,310 | B2 | 3/2016 | Patel | |
| 9,358,636 | B2 | 6/2016 | Hammann | |
| 2002/0039186 | A1 | 4/2002 | Rosenberg | |
| 2002/0144458 | A1 | 10/2002 | Hunter | |
| 2003/0095266 | A1 | 5/2003 | Detalle | |
| 2003/0216875 | A1 | 11/2003 | Sakurai | |
| 2004/0156616 | A1* | 8/2004 | Strub .................. | G11B 27/031<br>386/224 |
| 2007/0218556 | A1 | 9/2007 | Harris | |
| 2007/0229834 | A1 | 10/2007 | Patel | |
| 2008/0003339 | A1 | 1/2008 | Johnson | |
| 2008/0093775 | A1 | 4/2008 | Menoni | |
| 2008/0124433 | A1 | 5/2008 | Yelden | |
| 2008/0204757 | A1 | 8/2008 | Manning | |
| 2008/0253648 | A1 | 10/2008 | Mulder | |
| 2009/0316927 | A1 | 12/2009 | Ferrill | |
| 2010/0070197 | A1 | 3/2010 | Wang | |
| 2010/0297671 | A1 | 11/2010 | Tschmelak | |
| 2011/0033062 | A1 | 2/2011 | Deng | |
| 2011/0088477 | A1 | 4/2011 | Someda | |
| 2012/0002193 | A1 | 1/2012 | Elliott | |
| 2012/0008802 | A1 | 1/2012 | Felber | |
| 2012/0014534 | A1 | 1/2012 | Bodley | |
| 2012/0020485 | A1 | 1/2012 | Visser | |
| 2012/0099732 | A1 | 4/2012 | Visser | |
| 2012/0202277 | A1 | 8/2012 | Wagner | |
| 2012/0206722 | A1 | 8/2012 | Grigoropoulos | |
| 2012/0234102 | A1 | 8/2012 | Johnson | |
| 2012/0314214 | A1 | 12/2012 | Alexander | |
| 2013/0058514 | A1 | 3/2013 | Akino | |
| 2013/0118227 | A1 | 5/2013 | Sakaibara | |
| 2013/0150114 | A1 | 6/2013 | Bodley | |

(56) References Cited

U.S. PATENT DOCUMENTS

| | | | |
|---|---|---|---|
| 2013/0201316 | A1 | 8/2013 | Binder |
| 2013/0228016 | A1* | 9/2013 | Sakurai ................ G01N 33/02 73/661 |
| 2013/0266925 | A1 | 10/2013 | Nunamaker |
| 2013/0344208 | A1 | 12/2013 | Singh |
| 2014/0011690 | A1 | 1/2014 | Dimov |
| 2014/0003819 | A1 | 2/2014 | Loeser |
| 2014/0079248 | A1 | 3/2014 | Short |
| 2014/0125965 | A1 | 5/2014 | Nagli |
| 2015/0204822 | A1 | 7/2015 | Horan |
| 2017/0027168 | A1 | 2/2017 | Heath |

FOREIGN PATENT DOCUMENTS

| | | |
|---|---|---|
| DE | 19716672 | 6/1998 |
| DE | 69320728 | 1/1999 |
| DE | 10315541 | 10/2001 |
| DE | 102005051643 | 4/2006 |
| DE | 102006035730 | 1/2008 |
| EP | 0829225 A2 | 3/1998 |
| EP | 1348955 | 10/2003 |
| ES | 2147141 | 8/2000 |
| JP | 2004085303 A * | 3/2004 |
| JP | 2004085303 A | 3/2004 |
| JP | 2009008696 | 1/2009 |
| UA | 104233 | 1/2014 |
| WO | 9425851 | 11/1994 |
| WO | 9857145 | 12/1998 |
| WO | 9915890 | 4/1999 |
| WO | 02057774 | 7/2002 |
| WO | 02079765 | 10/2002 |
| WO | 2009047549 | 4/2009 |
| WO | 2013004210 | 1/2013 |
| WO | 2014180568 | 11/2014 |

OTHER PUBLICATIONS

Mohamed, Abdellatif et al., "Estimation of HRW wheat heat damage by DSC, capillary zone electrophoresis, photoacoustic spectroscopy and rheometry"—Science Direct (19 pages).

Aguilera, Jose Miguel, "Why food microstructure?" J. Food Engineering 67 (2005) 3-11 (9 pages).

Chauvin, Maite A., et al., "Relationship Between Instrumental and Sensory Determination of Apple and Pear Texture," J. Food Quality, 33 (2010) 181-198 (18 pages).

Khairi, Mohd, "Contact and non-contact ultrasonic measurement in the food industry: a review", Measurement Science and Technology, vol. 27, No. 1, Dec. 1, 2015, abstract, 14 pages.

Abdel-Salam et al., "Qualitative evaluation of maternal milk and commerical infant formulas via LIBS" Talanta 115 (2013)422-426 (5 pages).

Applied Spectra, Inc.—Technique—Gate Delay, from http://www.appliedspectra.com/technology/gate-delay.html printed Sep. 29, 2014 (6 pages).

Assion et al., "Femtosecond laser-induced-breakdown spectrometry for Ca2+ analysis of biological samples with high spatial resolution," Appl Phys. 2003, 77:391-97.

Kongbonga et al., Classification of vegetable oils based on their concentration of saturated fatty acids using laser induced breakdown spectroscopy (LIBS), Food Chemistry 147 (2014) 327-331 (5 pages).

Berer et al., "Remote photoacoustic imaging for material inspection" 2nd International Symposium on Laser-Ultrasonics—Science, Technology and Applications, Journal of Physics: Conference Series 278 (2011) 012034 (4 pages).

Kowalczyk et al., "Bulk measurement of copper and sodium content in Culn0.7Ga0.3Se2 (CIGS) solar cells with nanosecond pulse length laser induce breakdown spectroscopy (LIBS)" Department of Physics and Astronomy, University of Hawaii, Jan. 8, 2013 (6 pages).

Lanza et al., "Calibrating the ChemCm laser-induced breakdown spectroscopy instrument for carbonate minerals on Mars" May 1, 2010, vol. 49, No. 13, Applied Optics (7 pages).

Lei et al., "Time-resolved characterization of laser-induced plasma from fresh potatoes" Spectrochimica Acta Part B 64 (2009) 891-898 (8 pages).

Menut et al., "Micor-laser-induced breakdown spectroscopy technique: a powerful method for performing quantitative surface mapping on conductive and nonconductive samples," Oct. 2003, Applied Optics, vol. 42, No. 3 0, pp. 6063-6071.

"NRC-CNRC ""Laser-Induced Breakdown Spectroscopy (LIBS) Optical Sensing Technology for Rapid On-site ChemicalAnalysis""" (4 pages)".

PCT International Search Report and Written Opinion for PCT/US2015/052510 dated Dec. 14, 2015 (9 pages).

Pedarnig, "Application of laser-induced breakdown spectroscopy to the analysis of secondary materials in industrial production" 2014 Woodhead Publishing Limited (26 pages).

Ravishankar, et al., "Photo-acoustic emission measurements in liquid-based food and aqueous products," 2007, 12 pages.

Samek et al., "Ultra-short laser puls ablation using shear-force feedback: Femtosecond laser induced breakdown spectroscopy feasability study," Spectrochimica Acta Part B, pp. 1225-1229.

Slaughter, "Nondestructive Quality of Measurement of Horticultural Crops," University of CA, Davis, 2011, 13 pages.

Sun et al., "Correction of self-absorption effect in calibration-free laser-induced breakdown spectroscopy by an internal reference method" Talanta 79 (2009) 388-395 (8 pages).

"TSI Laser Induced Breakdown Spectroscopy, Chemreveal LIBS Desktop Elemental Analyzer from http://www.tsi.com/ChemReveai-LIBS-Desktop-Analyzer/, printed Aug. 6, 2014 (3 pages)".

"What is LIBS from http://www.spectrolabsystems.net/products/analytical-instruments/laser-induced-breakdown . . . , printed Aug. 6, 2014(1 page)".

Cravetchi et al., "Scanning microanalysis of Al alloys by laser-induced breakdown spectroscopy" Spectrochimica Acta Part B 59 (2004) 1439-1450 (12 pages).

Kossakovski et al., "Topographical and Chemical Microanalysis of Surfaces with a Scanning Probe Microscope and Laser-Induced Breakdown Spectroscopy" Anal. Chem. 2000, 72, 4731-4737 (7 pages).

Chauvin et al., Standard Scales for Crispness, Crackliness and Crunchiness in Dry and Wet Foods: Relationship with Acoustical Determinations, Journal of Texture Studies, vol. 39, No. 4, Aug. 1, 2008, pp. 345-368.

De Belie et al., "Crispness Judgement of Royal Gala Apples Based on Chewing Sounds", Biosystems Engineering, Academic Press, UK, vol. 81, No. 3, Mar. 1, 2002, pp. 297-303.

Duizer et al., "A review of acoustic research for studying the sensory perception of crisp, crunchy and crackly textures", Trends in Food Science and Technology, Elsevier Science Publishers, GB, vol. 12, No. 1, Jan. 1, 2001, pp. 17-24.

Roudaut et al., "Crispness: a critical review on sensory and material science approaches", Trends in Food Science and Technology, Elsevier Science Publishers, GB, vol. 13, No. 6-7, Jun. 1, 2002, pp. 217-227.

European Patent Office, "Supplemental European Search Report" for related EP Application No. 17760967.4, dated Sep. 2019, 13 pages.

Patent Cooperation Treaty, "International Preliminary Report on Patentability," for related PCT Application No. PCT/US/2018/051779, dated Oct. 11, 2019, 30 pages.

Examination Report dated Dec. 7, 2020 in EP 17760967.4.

\* cited by examiner

1300

1700

1701 1702

1711

1712

| FOOD SNACK | FOOD COMPOSITE NUMBER RANGE |
|---|---|
| SOLID A | 5.3 - 6.3 |
| SOLID B | 7.2 - 7.6 |
| * | |
| * | |
| * | |
| * | |
| LIQUID A | 9.3 - 10.3 |
| LIQUID B | 14.2 - 14.6 |
| * | |
| * | |
| * | |
| * | |

QUANTITATIVE IN-SITU TEXTURE MEASUREMENT APPARATUS AND METHOD

CROSS-REFERENCE TO RELATED APPLICATIONS

The present invention claims priority to U.S. Provisional Application No. 62/303,511 filed Mar. 4, 2016. Additionally, the present invention claims priority to U.S. application Ser. No. 15/380,622 filed Dec. 15, 2016, which is a Continuation of U.S. application Ser. No. 14/864,593 filed Sep. 24, 2015, now U.S. Pat. No. 9,541,537 issued Jan. 10, 2017. Lastly, the present invention claims priority to U.S. application Ser. No. 14/864,728 filed Sep. 24, 2015.

FIELD OF THE INVENTION

The present invention relates to an in-situ quantitative measurement of texture for food products using acoustic techniques.

PRIOR ART AND BACKGROUND OF THE INVENTION

Prior Art Background

Texture is one of the most important sensory characteristics that determine consumer preference for food products and is usually assessed by sensory evaluation. However, sensory evaluation is time-consuming and expensive, and therefore, reliable and practical instrumental methods are needed to accurately predict sensory texture attributes and other food snack properties.

When a food snack such as potato chip is manufactured, textural properties are dependent on raw material characteristics (i.e. low solids or high solids potatoes) and the processing conditions that the raw material undergoes such as temperature profile, slice thickness, pulse electric field strength intensity and so on.

The crispiness, softness and/or crunchiness of a potato chip are just a few examples of texture and mouthfeel characteristics that make food appealing and satisfying to consumers. Texture is one of the major criteria which consumers use to judge the quality and freshness of many foods. When a food produces a physical sensation in the mouth (hard, soft, crisp, moist, dry), the consumer has a basis for determining the food's quality (fresh, stale, tender, ripe).

A major challenge is how to accurately and objectively measure texture and mouthfeel. Texture is a composite property related to a number of physical properties (e.g., hardness and fracturability), and the relationship is complex. Texture or mouthfeel cannot be quantitatively measured in a single value obtained from an instrument. Mouthfeel is hard to define as it involves food's entire physical and chemical interaction in the mouth—from initial perception on the palate, to first bite, through mastication and finally, the act of swallowing. There is a need to quantitatively measure the food interaction in the mouth.

A problem with hardness is that their correlations with sensory tests are not always as high as expected. In many instances, the metric of peak force exerted on a potato chip does not adequately replicate the energy experienced by consumers. Therefore, consumers' judgments of Hardness can be more nuanced than a simple peak force metric from a destructive analytical test.

Presently, there is no good correlation of any type between instrument readings and taste panel scores. The issue is that no instrument is capable of manipulating a food product precisely the same way as the human mouth during mastication. For example, an instrument may compress a food product between two plates, while a human would be biting down with incisors. Therefore, there is a need for a quantitative texture measurement that has a good correlation with a qualitative measurement from an expert panel.

Prior Art Texture Measurement System

An Universal TA-XT2 Texture Analyzer from Texture Technologies Corp. can perform a complete TPA calculation and comes with multiple standard probes, including various sizes of needles, cones, cylinders, punches, knives and balls. FIG. 1. Illustrates a prior art system for measuring texture attributes such as hardness and fracturability with a TA-XT2 Texture Analyzer. The system includes a probe (0101) that exerts a force on a food snack such as a potato chip and measure the amount of force required to break the chip. Hardness may be measured as a force required to deform the product to given distance, i.e., force to compress between molars, bite through with incisors, compress between tongue and palate.

Prior Art Texture Measurement Method

As generally shown in FIG. 2, a prior art texture measurement method associated with the prior art system may include the steps comprising:

(1) placing a food snack on a surface (0201);

(2) with a probe, exerting a force and break/deform the food snack (0202);

(3) generating an acoustic signal from the food snack or measuring the force exerted (0203);

Force exerted may depend on the shape of the food snack. For example, a U shaped food snack or a curvy shaped food snack may be placed in either direction and the force exerted to break the food snack may be different. Therefore, there is a need for a shape independent quantitative texture measurement.

(4) capturing the acoustic signal with an acoustic capturing device or record the force required to break the food snack (0204);

acoustic signal is captured for a period of time at preset frequencies and the signal is plotted as Time (seconds) vs. Intensity (dB). There is a need to measure acoustic signal in a wide range of frequencies.

(5) generating a texture model from the acoustic signal (0205); and

A model for texture attributes such as hardness and fracturability is developed from the Time vs. Intensity plot for the food snack. Alternatively, a model from measured force may also be used to develop a model.

(6) measuring the texture attribute of the food snack from the texture model.

Texture attributes of a food snack is measured from the model developed in step (0205). The texture attributes are correlated to a qualitative texture attributes number from an expert panel as described below in FIG. 3.

Prior Art Texture Correlation Method

As generally shown in FIG. 3, a prior art texture correlation method may include the steps comprising:

(1) shipping food snack samples to an expert panel (0301);

The shipping of the food snack samples may take time and the food snack may undergo texture change during the shipping process. Therefore, there is a need to limit the number of times food snacks are shipped the expert panel.

(2) qualitatively analyzing the food snack samples (0302);

The process starts with a well-trained sensory panel to carry out a meaningful texture profile analysis, a panel of judges needs to have prior rating knowledge of the texture classification system, the use of standard rating scales and the correct procedures related to the mechanics of testing. Panelist training starts with a clear definition of each attribute. Furthermore, the techniques used to evaluate the food product should be explicitly specified, explaining how the food product is placed in the mouth, whether it is acted upon by the teeth (and which teeth) or by the tongue and what particular sensation is to be evaluated. Panelists are given reference standards for evaluation so they can practice their sensory evaluation techniques and the use of scales. Hardness and fracturability are usually considered to be the most important texture attribute. Presently there is no good correlation of any type between instrument readings and taste panel scores. Presently there are no instruments capable of manipulating a food product precisely the same way as the human mouth during mastication. For example, an instrument may compress a food product between two plates, while a human would be biting down with incisors. In fact, what an instrument measures may not relate at all to what the consumer perceives. Therefore, there is a need to have a system that can quantitatively measure texture attributes and correlate to the taste panel scores.

(3) assigning a descriptive panel number for the texture attributes of the food snack sample (0303);

An organoleptic sensory evaluation is performed in which the trained panelists assign intensity levels on various descriptors/texture attributes. For example, for evaluating the potato chips, hardness may be considered one important attribute. In this case, panelists assign a hardness score based on a scale, where 1 equals extremely soft and 15 equals extremely hard. The panelists may rate the hardness of potato chip samples A, B and C's. After taste paneling is complete, instrument readings of the food product are made as described below in step (0304).

(4) measure texture attributes using an invasive analytical method (0304);

There is a need that the instrumental technique selected duplicates as closely as possible how the mouth manipulates the particular food product. The instrument should apply the same amount of force in the same direction and at the same rate as the mouth and teeth do during mastication. The instrument may record acoustic signals for a period of time and generate a model. However, current instruments are limited by recording acoustics at discrete frequencies. Therefore, there is a need for recording sound in a wider frequency range.

(5) correlate the analytical and the qualitative texture attributes (0305); and Statistically correlate between sensory data (descriptive panel number) and instrumental measurements. For example, prior art adjusted $R^2$ correlation numbers are in the range of 0.5-0.65. Therefore, there is a need for a strong correlation between descriptive panel number and the analytical model.

(6) generating a correlation model (0306).

Current objective methods to measure texture are limited in detecting textural changes of a small magnitude with an acceptable degree of accuracy and require several measurements of the same substrate to differentiate slightly different substrate with statistical significance. Currently in the food industry snacks and beverages textures are characterized either by measuring the force and gradient to make a substrate fail or by rheological means. In snacks, the TAXT2 is a well-known apparatus to measure force and gradient as a substrate fails; for beverages sometimes a rheometer is utilized to measure the viscosity or elasticity of fluid. While both types of measurement have been of vital importance to the industry, they do not explain the change in force/gradient, rheology, mouthfeel, or interaction within a mouth the consumer experiences when the sample comes into contact with human saliva. Therefore there is a need to provide a quantitative model may be correlated through an 'in-situ' measurement.

Consequently, there is a need for a quantitative texture measurement that accomplishes the following objectives:

Provide a quantitative method to measure finished product attributes such as oil content, moisture, slice thickness, and salt content.

Provide for quantitative analytical measurement of the textural attributes such as hardness, fracturability, crispiness, and surface oiliness.

Provide for an in-situ method to quantitatively measure consumer experience of eating a sample when the sample comes into contact with human saliva.

Provide for an in-situ method to quantitatively texture attributes that is calibrated to the characteristics (viscosity and pH) of human saliva.

Provide for frequency domain data to accurately model the texture attributes.

Provide for acoustic signal capture in a broad frequency range from 0 to 5000 KHz.

Provide for shape independent quantitative test for texture measurement.

Provide for a quantitative measurement of texture of a food snack from initial perception on the palate, to first bite, through mastication and finally, the act of swallowing.

Provide for quantitative measurement of texture with minimum samples with greater accuracy and reliability.

Provide for a less expensive quantitative texture measurement test.

Provide for instant results of the quantitative measurement.

Provide for repeatable and reproducible quantitative measurements of food snacks.

Provide a method to fingerprint food snacks with a quantitative measurement of food property.

While these objectives should not be understood to limit the teachings of the present invention, in general these objectives are achieved in part or in whole by the disclosed invention that is discussed in the following sections. One skilled in the art will no doubt be able to select aspects of the present invention as disclosed to affect any combination of the objectives described above.

BRIEF SUMMARY OF THE INVENTION

The present invention in various embodiments addresses one or more of the above objectives in the following manner.

The apparatus includes an acoustic capturing device and a data processing unit. When a human being eats/drinks a food snack, the physical interaction in the mouth sends pressure waves that propagate through the ear bone and produce an acoustic signal. The acoustic capturing device records and forwards the signal to a data processing unit. The data processing unit further comprises a digital signal processing module that smoothens, transforms and filters the received acoustic signal. A statistical processing module further filters the acoustic signal from the data processing unit and generates a quantitative acoustic model for texture attributes such as hardness and fracturability. The quantitative model is correlated with a qualitative texture measurement from a descriptive expert panel. Another method includes a food snack fingerprinting using an in-situ quantitative food property measurement.

The present invention system may be utilized in the context of method of quantitatively measuring texture of a food snack, the method comprises the steps of:

(1) eating/drinking a food snack;
(2) generating an acoustic signal from eating/drinking the food snack;
(3) capturing the acoustic signal with an acoustic capturing device;
(4) forwarding the acoustic signal to a data processing unit; and
(5) measuring the texture attributes of the food snack with an in-situ acoustic texture model.

Integration of this and other preferred exemplary embodiment methods in conjunction with a variety of preferred exemplary embodiment systems described herein in anticipation by the overall scope of the present invention.

BRIEF DESCRIPTION OF THE DRAWINGS

For a fuller understanding of the advantages provided by the invention, reference should be made to the following detailed description together with the accompanying drawings wherein:

FIG. 17 is an exemplary food snack fingerprinting matching table according to a preferred exemplary embodiment.

DESCRIPTION OF THE PRESENTLY EXEMPLARY EMBODIMENTS

Figure 1:
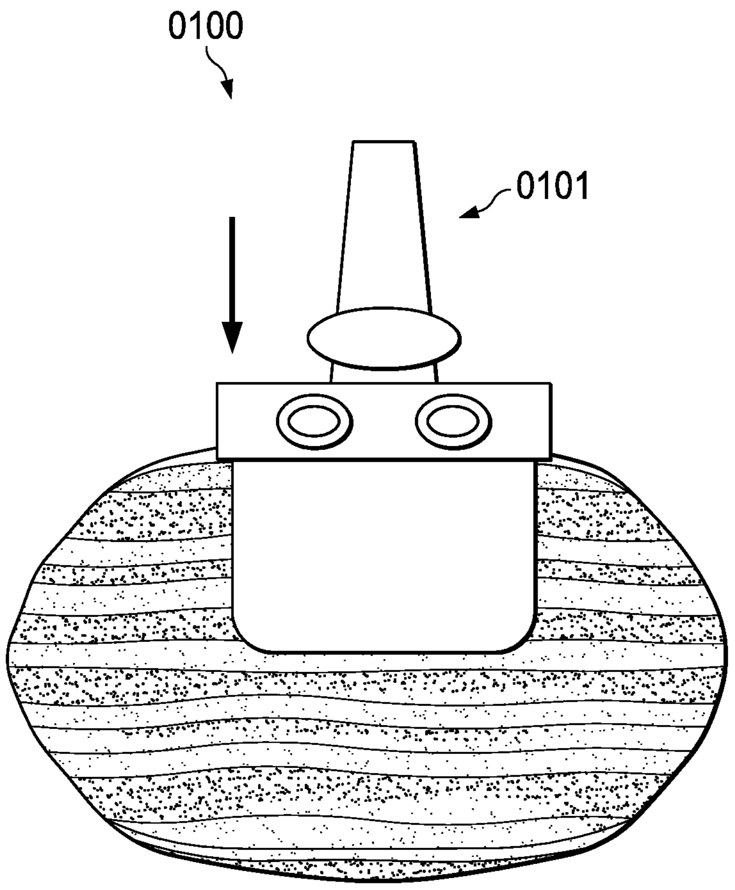
FIG. 1 is a prior art destructive system for measuring texture in food products.
Figure 2:
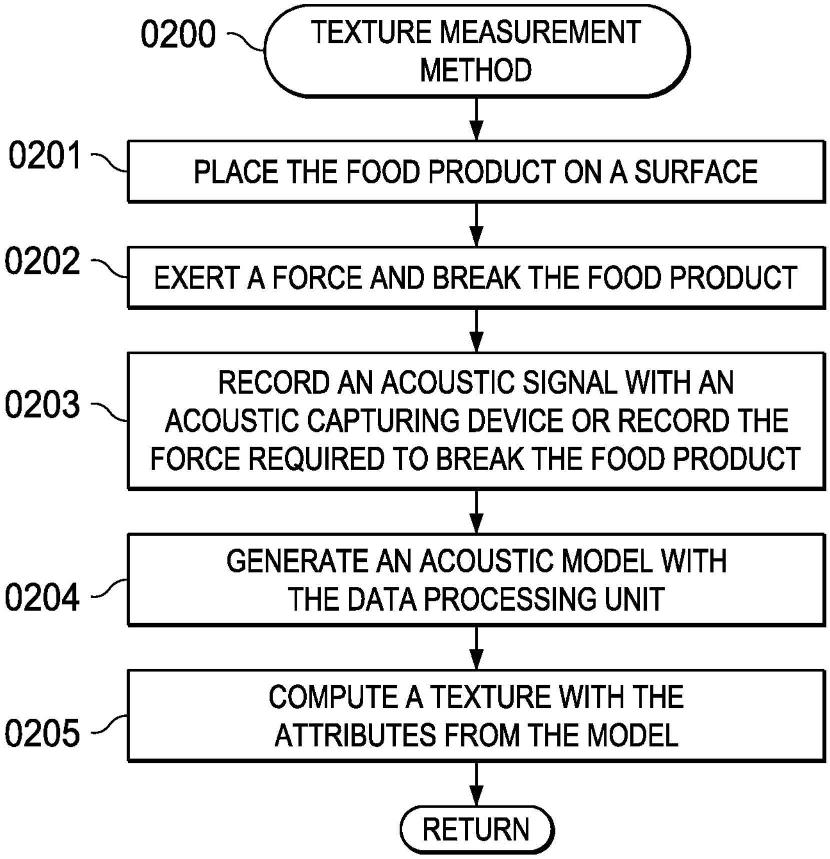
FIG. 2 is a prior art chart for measuring texture with acoustic signals.
Figure 3:
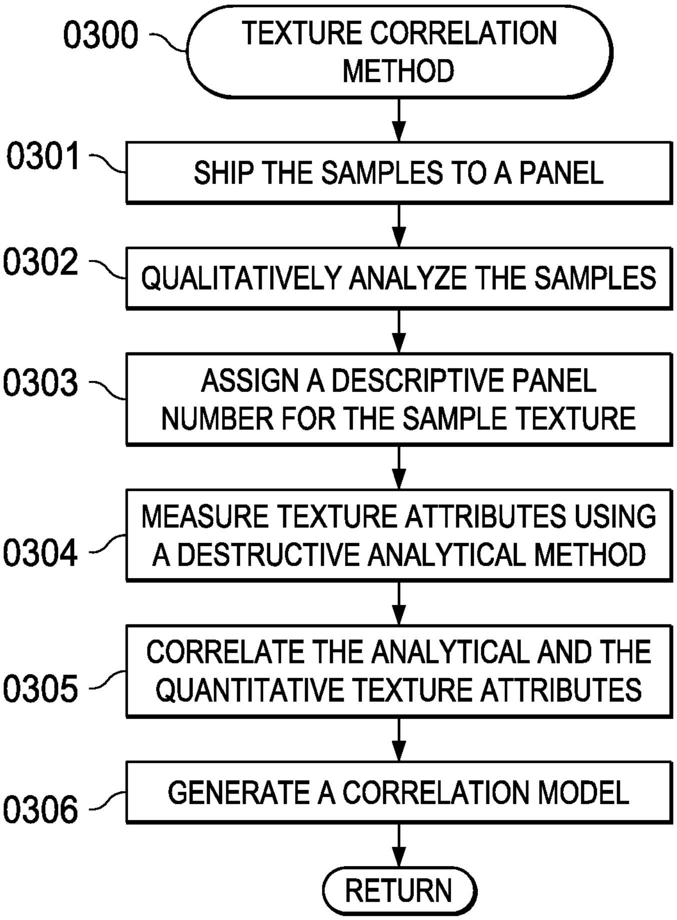
FIG. 3 is a prior art method for correlating texture measurements.

While this invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described with particular reference to the presently exemplary embodiment, wherein these innovative teachings are advantageously applied to in-situ quantitative measurement of texture attributes for food snacks apparatus and method. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

The term “texture” as used herein is defined a composite property related to a number of physical properties such as hardness, fracturability, tooth-pack, roughness of mass, moistness of mass, residual greasiness, surface roughness, and surface oiliness. It should be noted that the term “texture” and “texture attribute” is used interchangeably to indicate one or more properties of texture. It should be noted that the terms “descriptive panel number”, “taste panel score”, “qualitative texture number” and “taste panel number” are used inter-changeably to indicate a qualitative measurement of texture measurements by an expert panel. It should be noted that the terms "in-situ acoustic model," "acoustic model," "acoustic texture model," and "quantitative texture attribute model," are used inter-changeably to indicate a quantitative model for a texture attribute of a food snack. The term texture as used herein with respect to a liquid or a beverage refers to properties such as viscosity, density, rheology and/or mouthfeel.

Exemplary Embodiment System for Quantitative Measurement of Texture Attributes (0400-0900)

One aspect of the present invention provides an in-situ method to quantitatively measure the texture attributes of food snacks. Another aspect of the present invention involves correlating the in-situ quantitative texture attribute measurement to a qualitatively measured texture attribute by an expert panel. The present invention is also directed towards developing a texture attribute model based on relevant frequencies in a captured acoustic signal. According to yet another aspect of the present invention, food snacks are identified ("food finger printing") based on an in-situ quantitative food snack property measurement.

Applicants herein have created a system that comprises an acoustic capturing device for recording/capturing an acoustic signal from a food snack and a data processing unit that processes the captured acoustic signal and generates a texture attribute model. There are a number of embodiments of this invention which fall within the scope of the invention in its broadest sense.

Exemplary Embodiment In-Situ System (0400-0600)

Figure 4:
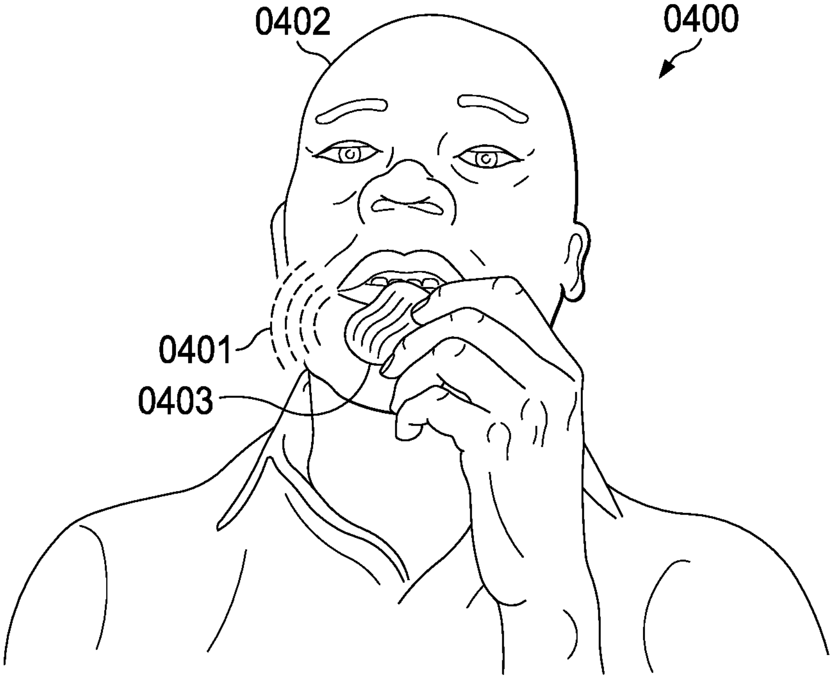
FIG. 4 is a system for eating food snacks according to an exemplary embodiment of the present invention.

FIG. 4 (0400) generally illustrates a physical interaction of a human being (0402) interacting with a food snack (0403) that produces an acoustic signal (0401). The physical and chemical interaction in the mouth include steps from initial perception on the palate, to first bite, through mastication and finally, to the act of swallowing. According to an exemplary embodiment, the acoustic signal (0401) generated from the consumption (eating or drinking or chewing) of a food snack (0403) by a human being is recorded/captured by an acoustic capturing device. A headset is ergonomically positioned on the temple and cheek and the electromechanical transducer, which converts electric signals into mechanical vibrations, sends sound to the internal ear through the cranial bones. Likewise, a microphone may be used to record spoken sounds via bone conduction. According to another preferred exemplary embodiment, the food snack is a solid. According to yet another preferred exemplary embodiment, the food snack is a liquid. For example, the solid food snack may be a potato chip or a cheese puff. The liquid may be a cold beverage, wine or hot liquids such as coffee or soup. The food snack may also be a semi-solid. Currently in the food industry snacks and beverages textures are characterized either by measuring the force and gradient to make a substrate fail or by rheological means. Saliva is a watery substance located in the mouths of humans and animals, secreted by the salivary glands. Human saliva is 99.5% water, while the other 0.5% consists of electrolytes, mucus, glycoproteins, enzymes, antibacterial, and bacteria compounds such as secretory IgA and lysozyme. The enzymes found in saliva are essential in beginning the process of digestion of dietary starches and fats. Furthermore, saliva serves a lubricative function, wetting food and permitting the initiation of swallowing, and protecting the mucosal surfaces of the oral cavity from desiccation. While the characteristic of saliva such as pH, viscosity and others are different from individual to individual, some exemplary embodiments enable a means to 'calibrate' the measurement with snacks or beverage 'standards.' According to a preferred exemplary embodiment, when a food or beverage item is consumed information on texture information may be captured with the acoustic fingerprint of each food and beverage item include the interaction with saliva. As an example, differentiating sweeteners at the concentrations that are found in beverages in a rheological manner can prove to be very difficult; in other words to distinguish the viscosity of a Diet Pepsi® vs. a regular Pepsi® is difficult given the measurement error; however, when in contact with saliva, different sweeteners can have different interactions with human saliva given their chemical composition, the mixture of the beverage and the saliva produces viscosity differences that can be differentiated by an in-situ model and texture measurement as described in more detail in FIG. 10 (1000).

Figure 5:
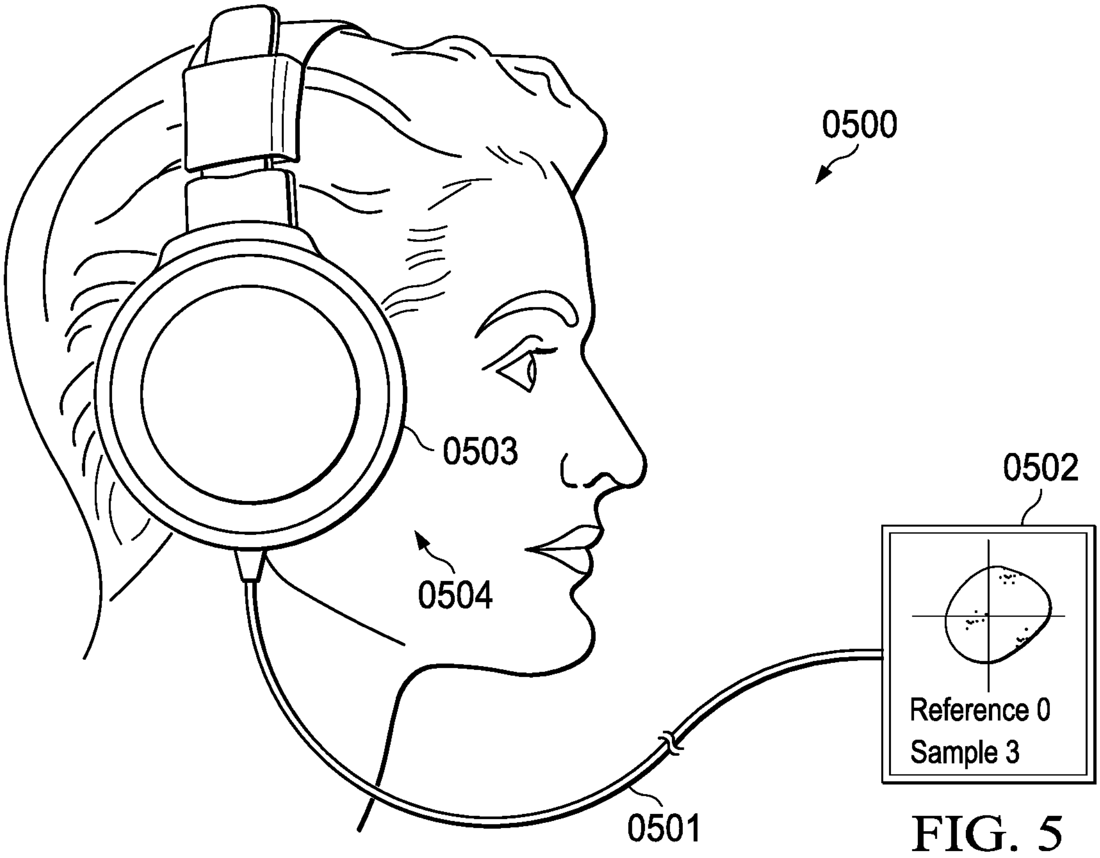
FIG. 5 is an acoustic capturing unit that captures acoustics from a human being eating a food snack according to an exemplary embodiment of the present invention.

The present invention may be seen in more detail as generally illustrated in FIG. 5, wherein a system (0500) includes an acoustic capturing device (0503) that records an acoustic signal from a physical consumption of a food snack in a human being (0504). The acoustic signal may be forwarded to a data processing unit (0502) through a connecting element (0501). According to an exemplary embodiment, an acoustic capturing device (0503) may be positioned to record/capture an acoustic signal from the food snack. The acoustic capturing device may capture acoustic signals in the frequency range of 0 to 5000 KHz. A headset may be ergonomically positioned on the temple and cheek and an electromechanical transducer, which converts electric signals into mechanical vibrations, sends sound to the internal ear through the cranial bones. Likewise, a microphone can be used to record spoken sounds via bone conduction. The acoustic capturing device may be physically connected to a data processing unit (0502) or wirelessly connected. The wired connecting element may be a hi-definition audio cable that can transmit data without substantial signal loss. A texture model generator may display data from the data processing unit (0502). The in-situ texture model generator may be integrated into the data processing unit (DPU) (0502).

The acoustic capturing device (0503) may be connected physically with a conducting cable to the DPU (0502) via an input-output module in the DPU (0502). In an alternate arrangement, the acoustic capturing device (0503) may forward an acoustic signal to the input-output module in the DPU (0404) wirelessly. The wireless protocol may use standard protocols such as WIFI or Bluetooth. In an exemplary embodiment, the acoustic capturing device (0503) may be remotely located and the acoustic signal may be forwarded wirelessly to the DPU (0502) with a protocol such as LTE, 3G and/or 4G. In another exemplary embodiment, the remotely located DPU (0502) may be connected to the acoustic capturing device (0503) with wired protocol such as Ethernet. The acoustic capturing device may capture the acoustic signal across a wide range of frequencies. Additionally, the acoustic capturing device may be placed an angle directly in front of the human being. According to a preferred exemplary embodiment, the acoustic capturing device captures acoustic signals in a unidirectional manner. According to another preferred exemplary embodiment, the acoustic capturing device captures acoustic signals in omnidirectional manner. The acoustic capturing device may forward the captured acoustic signal to a processing device physically through a cable. According to a preferred exemplary embodiment, the acoustic capturing device is a wireless microphone that contains a radio transmitter. In a preferred exemplary embodiment, the acoustic capturing device is a dynamic microphone. In another preferred exemplary embodiment, the acoustic capturing device is a fiber optic microphone. A fiber optic microphone converts acoustic waves into electrical signals by sensing changes in light intensity, instead of sensing changes in capacitance or magnetic fields as with conventional microphones. The acoustic capturing device may use electromagnetic induction (dynamic microphones), capacitance change (condenser microphones) or piezoelectricity (piezoelectric microphones) to produce an electrical signal from air pressure variations. The microphones may be connected to a preamplifier before the signal can be amplified with an audio power amplifier or recorded. The microphones may be regularly calibrated due to the sensitivity of the measurement. In another preferred exemplary embodiment, the acoustic capturing device has a digital interface that directly outputs a digital audio stream through an XLR or XLD male connector. The digital audio stream may be processed further without significant signal loss.

According to a preferred exemplary embodiment, the acoustic signal may then be captured for a period of time. The acoustic signal may be represented as Intensity (dB) vs. Time (secs). According to a preferred exemplary embodiment, the acoustic signal is captured for 1 sec to 5 minutes. According to yet another preferred exemplary embodiment, the acoustic signal from the food snack is captured for 2 sec. According to a more preferred exemplary embodiment, the acoustic signal from the food snack is captured for 1 sec. According to a most preferred exemplary embodiment, the acoustic signal from the food snack is captured for 10 sec.

According to a preferred exemplary embodiment, the food snack may be processed in a human mouth for 1 sec to 3 minutes. According to yet another preferred exemplary embodiment, the food snack may be processed in a human mouth less than second. According to a more preferred exemplary embodiment, the food snack may be processed in a human mouth for greater than 3 minutes. According to a most preferred exemplary embodiment, the food snack may be processed in a human mouth for 10 seconds to 20 seconds. According to another most preferred exemplary embodiment, the food snack may be processed in a human mouth for 5 seconds to 10 seconds.

Figure 10:
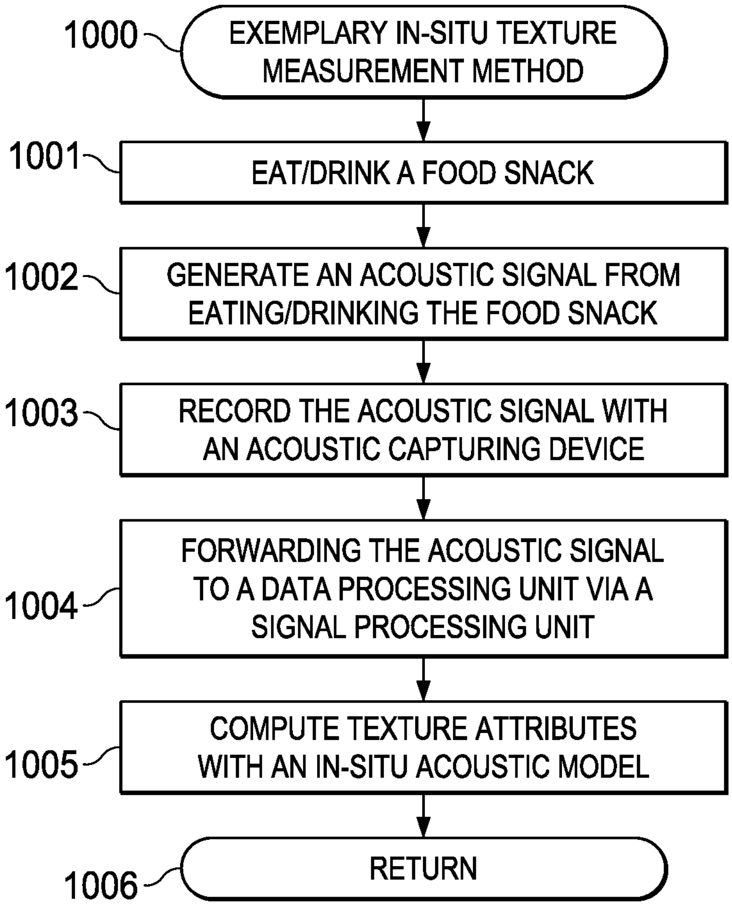
FIG. 10 is a flow chart method for quantitative measurement of texture according to an exemplary embodiment of the present invention.

The acoustic model may be developed using the method described in more detail in FIG. 10 (1000). The model may be programmed into the tool such as tool (0502) for measuring one or more texture attributes such as hardness, fracturability and denseness. An acoustic model for texture attribute hardness may be described below:

$$\text{Hardness}=f(X_{1\text{-}n},I_{1\text{-}n})$$

$$\text{Hardness}=I_1C_1+I_2C_2+I_3C_3+\ldots I_nC_n \quad (1)$$

Figure 12:
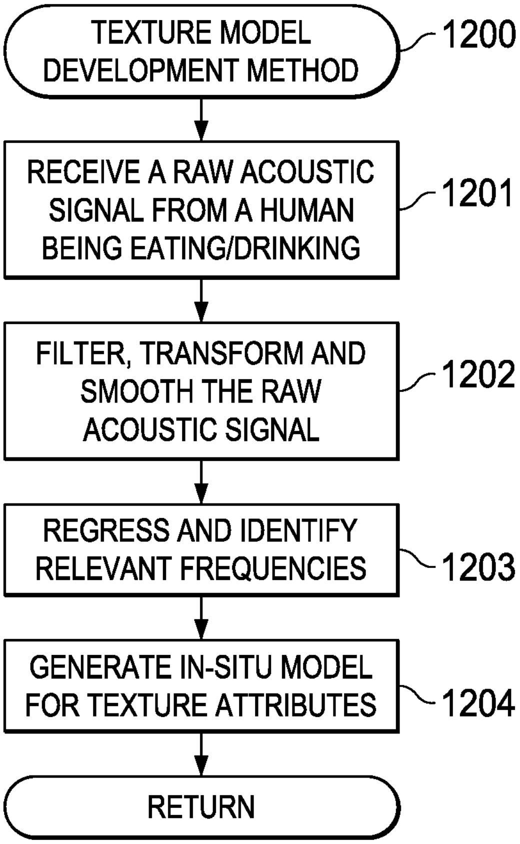
FIG. 12 is an exemplary flow chart method for quantitative texture model development according to a preferred embodiment of the present invention.

Where, $I_n$ is an intensity associated with a frequency $X_n$ $C_n$ is a coefficient associated with the frequency $X_n$ Coefficients ($C_1$-$C_n$) are determined using the method described in FIG. 12 (1200). A signal processing unit in the texture measurement tool (1306) identifies the relevant frequencies ($X_n$) and associated intensities ($I_n$). The tool (1306) may calculate a texture attribute such as hardness from the above model 1 by substituting the coefficients values ($C_1$-$C_n$) from a stored table for the food snack and the intensities ($I_n$) from the processed acoustic signal. Similarly, other texture attribute such as fracturability and denseness may be calculated from their respective models comprising the respective coefficients. It should be noted that even though the above represented model (1) shows a linear relationship between the texture attribute and intensities, a quadratic or polynomial model may also be represented to calculate the texture attributes. The hardness may also be compensated for changes in the characteristics of the human saliva when the food snack is consumed.

Similar acoustic models may be developed for models for other food properties such a moisture, solids content, oil content, slice thickness, density, blister density and topical seasonings. The relevant frequencies and associated intensities and the coefficients of the developed model may change depending on the food property. A generic model that may represent a food property may be described below:

$$\text{Food property}=f(Z_{1\text{-}n},P_{1\text{-}n})$$

$$\text{Food Property}=P_1D_1+P_2D_2+P_3D_3+\ldots P_nD_n \quad (2)$$

Figure 9:
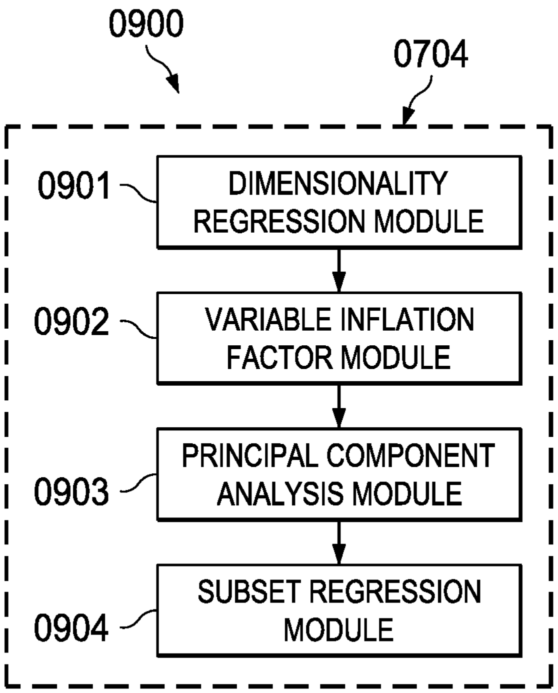
FIG. 9 is a statistical processing unit according to an exemplary embodiment of the present invention.

Where, $I_n$ is an intensity associated with a frequency $X_n$ $C_n$ is a coefficient associated with the frequency $X_n$ Coefficients ($D_1$-$D_n$) are determined using the energy excitation method described in FIG. 9 (0900). A signal processing unit in the texture measurement tool (1306) identifies the relevant frequencies ($Z_n$) and associated intensities ($P_n$). In addition to texture attribute, the tool (1306) may calculate a food property from the above model (2) by substituting the coefficients values ($D_1$-$D_n$) from a stored table for the food snack and the intensities ($P_n$) from the processed acoustic signal. The food properties may include Solids content, Moisture, Density, Oil content, Slice thickness, Seasoning particle size, and elements such as sodium, calcium, copper, zinc, magnesium, and potassium.

It should be noted that even though the above represented model (1) shows a linear relationship between the texture attribute and intensities, a quadratic or polynomial model may also be represented to calculate the texture attributes. The food property may also be compensated for changes in the characteristics of the human saliva when the food snack is consumed. A table (table 1.0) may be used to measure food properties as shown below from a captured and processed acoustic signal. The values shown below in table 1.0 are for illustration purposes only and should not be construed as a limitation.

TABLE 1.0

| Food Property | Relevant Frequencies ($Z_n$) | Intensities ($P_n$) | Coefficients ($D_n$) | Value | Limits |
|---|---|---|---|---|---|
| Texture | 14000 Hz | 68 | 3.5 | 7 | 4 to 10 |
| Attribute | 15000 Hz | 71 | 2.3 | | |
| Solids | 16000 Hz | 75 | 1.1 | 17 | 12 to 25 |
| content | 33,000 Hz | 77 | 9.0 | | |
| Density | 88000 Hz | 83 | 8.2 | 1.3 | 1 to 12 |
| Viscosity | 16000 Hz | 59 | 2.5 | 36% | 20% to 46% |
| | 49,000 Hz | 70 | 2.9 | | |
| Slice thickness | 76000 Hz | 64 | 4.3 | 0.055 | 0.035 to 0.075 |
| Rheology/ Mouth Feel | 64000 Hz | 74 | 8.8 | 0.5% | 0.1% to 15% |

Exemplary Food Snack Finger Printing System Embodiment (0600)

Figure 6:
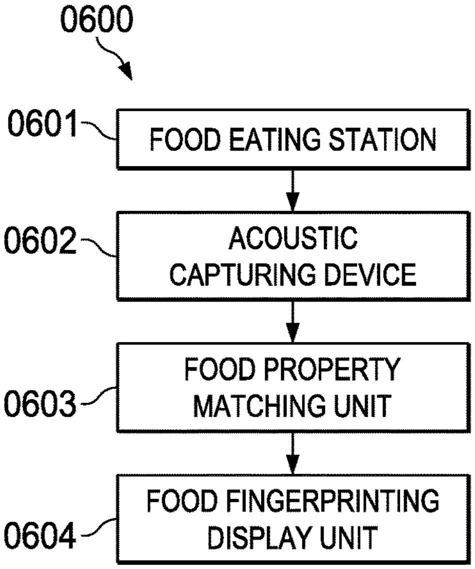
FIG. 6 is an in-situ system for measuring texture attributes according to an exemplary embodiment of the present invention.

As generally illustrated in FIG. 6, a food snack finger printing system comprises a food eating/drinking station (0601), an acoustic capture device (0602), a food property matching unit (0603) and a food finger printing display unit (0604). According to a preferred exemplary embodiment, a food snack is identified (finger printed) by matching a measured acoustic food property with an in-situ quantitative acoustic method, to an entry in a database, the database comprising a list of food snacks with associated food property ranges. The food property may be any property related to the food snack. According to a preferred exemplary embodiment, the food property may be a texture attribute such as hardness, fracturability, tooth-pack, roughness of mass, moistness of mass, residual greasiness, surface roughness, surface oiliness, and combinations thereof. The food property may also be moisture in the food snack, brittleness, crispiness, solids content and so on. According to yet another preferred exemplary embodiment, the food property is a liquid property such as viscosity, rheology, density, and so on. The database comprising a list of food snacks with associated food property ranges may be maintained in a local computer database or remotely in a network storage database. New food snacks may be added to the database as more in-situ quantitative models are developed. A more detailed description of the database is further described in FIG. 17 (1700).

Exemplary Data Processing Unit (0700)

Figure 7:
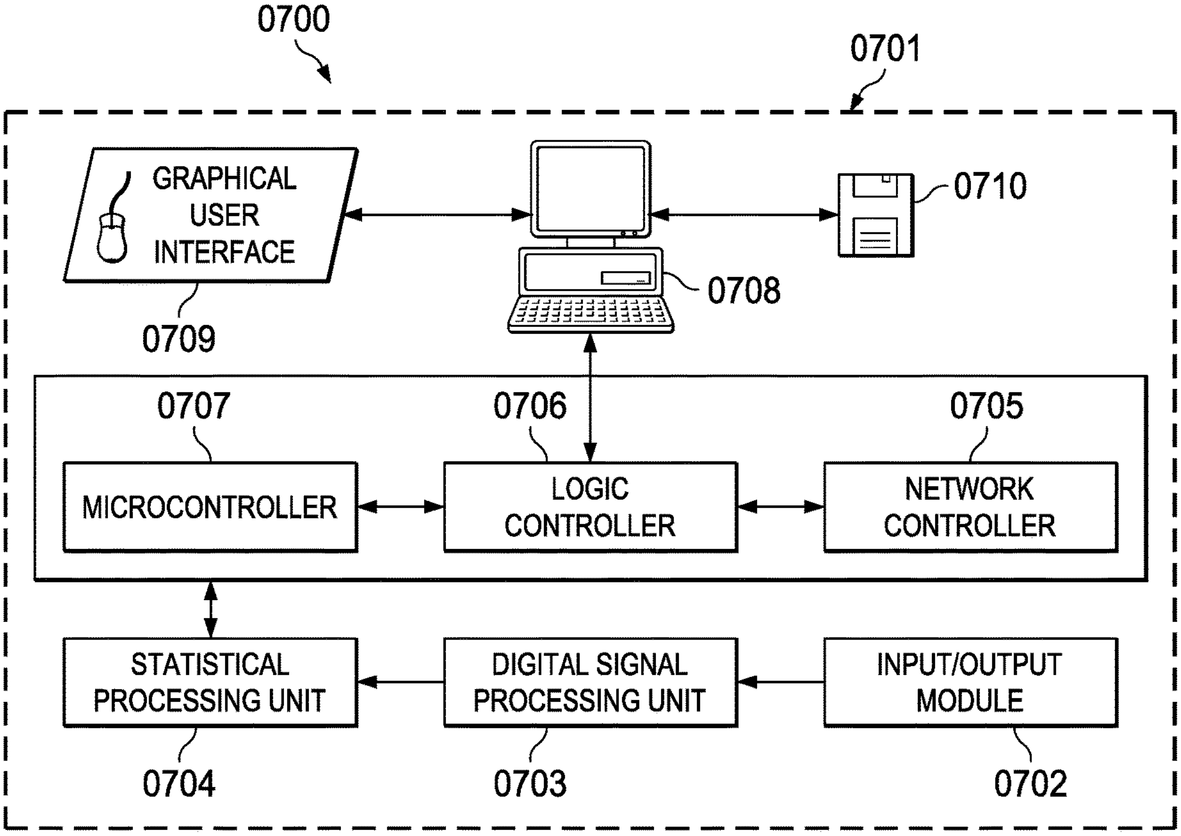
FIG. 7 is a data processing unit according to an exemplary embodiment of the present invention.

As generally illustrated in FIG. 7 (0700), a data processing unit (DPU) (0701) comprises a control unit, a display unit, a processing unit and an input output module. The control unit may further comprise a microcontroller (0707), a logic controller (0706), and a network controller (0705). The display unit may be connected to the control unit via a host bus. The display unit may further comprise a display terminal (0708) that is configured to display a graphical user interface (GUI) (0709). The GUI (0709) may be navigated with a pointing device or through a keyboard connected to the DPU. The GUI (0709) may be used to input parameters such as food snack specific frequencies, acoustic capture time, acoustic capture frequency range.

The processing unit may include a digital signal processing unit (0703) and a statistical processing unit (0704). The digital signal processing unit (0703) may get input from an input-output module (0702). The statistical processing unit (0704) may receive input from the digital processing unit (0703) and further process the input to find relevant frequencies for generating a quantitative acoustic model for a food snack. When an acoustic capturing device captures an acoustic signal, the signal may be forwarded to the DPU (0701) via the input-output module (0702). The input output module (0702) may further comprise a customized hardware such an analog to digital convertor (ADC) for capturing and processing a captured acoustic signal. The acoustic signal may be forwarded to the DPU using a wired or a wireless connection. The connection protocol and connecting conducting wires may be chosen such that there is minimum loss of signal and the signal to noise ratio is acceptable for further processing. A general purpose bus may carry data to and from different modules of the DPU (0701). It should be noted that the operation of the bus is beyond the scope of this invention.

The microcontroller (0707) may perform instructions from a memory or a ROM (0710). The instruction set of the microcontroller may be implemented to process the data of the acoustic signal. A custom instruction set may also be used by the microcontroller to prioritize and expedite the processing of the acoustic signal in real time during a manufacturing operation. The customization of the instruction set is beyond the scope of this invention. The logic controller may perform operations such as sequencing, prioritization and automation of tasks. The logic controller may also oversee the hand shake protocol for the bus interface. According to an exemplary embodiment, the logic controller controls the logic for identifying relevant frequencies in an acoustic signal. The logic controller may comprise a matching module that contains predefined frequencies for a plurality of food snacks. The logic controller may subsequently match the captured frequencies in the acoustic signal and quickly determine the texture of the food snack and the quality of the texture. For example, the matching module may include specific frequencies such as 14000 Hz and 75000 Hz. When a recorded acoustic signal comprises the frequencies 14000 Hz or 75000 Hz, then the logic controller may determine a match and alert the microcontroller with an interrupt signal. The microcontroller may then display the texture information on the display (0708) via GUI (0709). The logic controller may further continuously monitor the state of input devices and make decisions based upon a custom program to control the state of output devices.

Exemplary Digital Signal Processing Module (0800)

Figure 8:
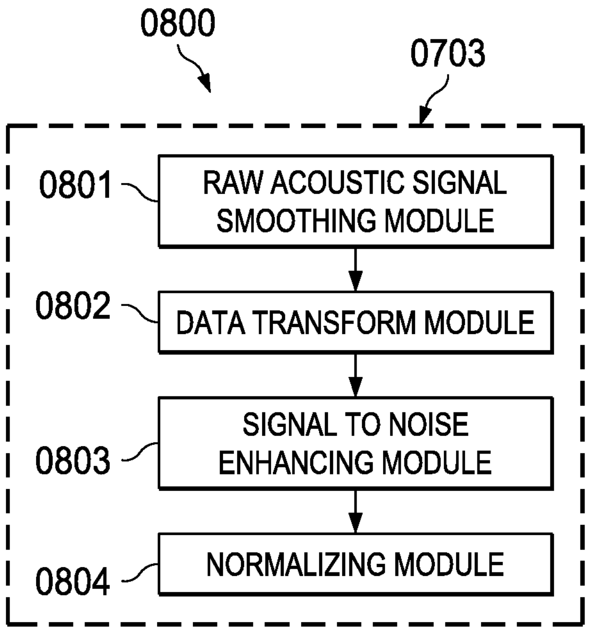
FIG. 8 is a digital signal processing unit according to an exemplary embodiment of the present invention.

Similar to the digital signal processing unit (0703) shown in FIG. 7 (0700), a digital signal processing unit (DSP) (0800) is generally illustrated in FIG. 8 (0800). The DSP (0800) may further comprise a smoothing module (0801), a data transformation module (0802), a signal to noise enhancing module (0803) and a normalization module (0804).

According to an exemplary embodiment, the acoustic smoothing module (0801) receives input from an input-module in a data processing unit and smoothens the received raw acoustic signal. Acoustic signals are inherently noisy and the data is discrete. The acoustic signals may be represented as Intensity (dB) vs. Time (secs or micro seconds). The data is made continuous by applying a windowing function to the discrete data. Windowing functions that may be applied to the discrete data may include Barlett, Blackmon, FlatTop, Hanning, Hamming, Kaiser-Bessel, Turkey and Welch windowing functions. A smoothing window with good frequency resolution and low spectral leakage for a random signal type may be chosen to smoothen the data. It should be noted that any commonly known windowing function may be applied to a raw acoustic signal to smoothen and interpolate the raw acoustic data.

Figure 18:
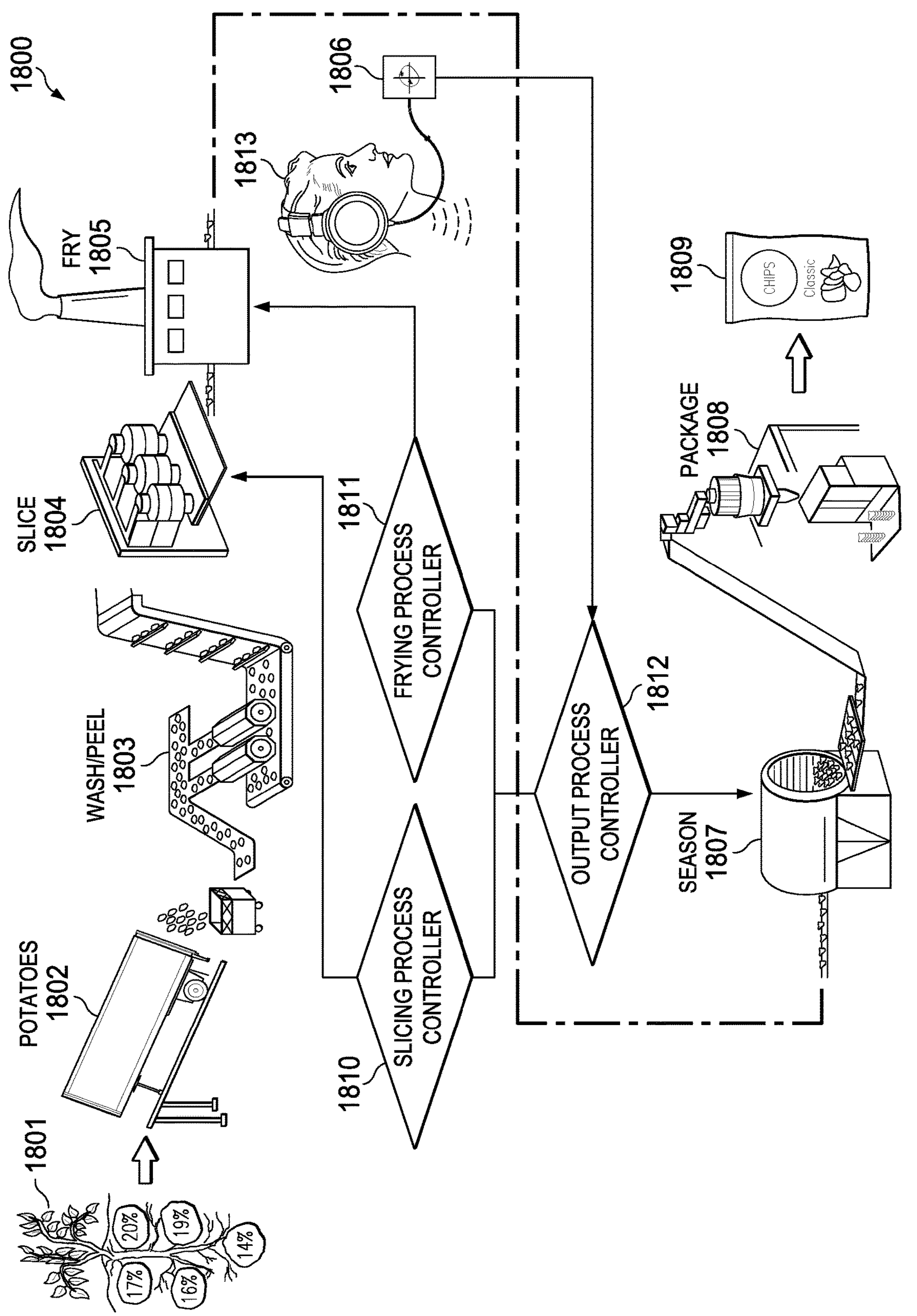
FIG. 18 is an exemplary quantitative in-situ discrete texture feedback manufacturing system according to a preferred embodiment of the present invention.

The smoothened acoustic signal from the smoothing module (0801) may be forwarded to a data transformation module (0802). The data transformation module (0802) may transform the acoustic signal represented in time domain as Intensity (dB) vs. Time (secs) to frequency domain as Intensity (dB) vs. Frequency (Hz) as generally shown in FIG. 18 (1800). According to a preferred exemplary embodiment, the transformation of acoustic signal from a time domain representation to a frequency domain representation provides for accurately correlating texture attributes to the pertinent frequencies of a food snack. Combining multiple acoustic waves produces a complex pattern in the time domain, but the transformed signal using FFT clearly shows as consisting almost entirely of distinct frequencies. According to most preferred exemplary embodiment, a fast fourier transformation (FFT) technique may be used to transform the acoustic signal from a time domain representation to a frequency domain representation. An example of the transformation may be generally seen in FIG. 20 (2000).

The transformed frequency signal from the transformation module may be noisy. A signal to noise enhancement module (0803) may receive the transformed signal from the data transform module (0802) and enhance the signal-to-noise ratio of the signal for further processing. A technique for smoothing the data to increase the signal-to-noise ratio without greatly distorting the signal may be used. A process such as convolution may also be used to increase the signal-to-noise ratio. The convolution process may fit successive sub-sets of adjacent data points with a low-degree polynomial by the method of linear least squares. Normalization module (0804) may receive the enhanced signal-to-noise frequency domain signal from the signal to noise enhancement module (0803).

The DSP (0800) may also identify pertinent frequencies and associated intensities from the enhanced signal-to-noise frequency domain signal and store the information in a database. A texture attribute computing unit (0712) in the DPU (0701) may further retrieve the stored frequency and intensity information to compute a texture attribute of a food snack. After a photo acoustic model has been developed, the texture attribute computing unit (0712) may store coefficients for different food snacks. The texture attribute computing unit (0712) may then retrieve the stored coefficients and the stores frequency and intensity information to compute a texture attribute measurement or to fingerprint a food snack.

Exemplary Statistical Processing Unit (0900)

Similar to the statistical processing unit (0704) shown in FIG. 7 (0700), a statistical processing unit (SPU) (0900) is generally illustrated in FIG. 9. The SPU (0900) may further comprise a dimensionality regression module (0901), a variance inflation factor module (0902), a principal component analysis module (0903), and a subset regression module (0904).

The smoothened, transformed and normalized signal from the digital signal processing unit (0703) is forwarded to SPU (0704) for developing texture attribute model with good correlation. The high dimensionality of spectral data requires statistical filtering to build meaningful models. For example, the acoustically smoothed signal may be sampled at 512 linearly spaced frequencies, and each value may be averaged across replicates and used to create a statistical model. According to a preferred exemplary embodiment, the dimensionality regression module reduces the total frequencies of the spectral data to a reasonably acceptable number for model development with high correlation. According to another preferred exemplary embodiment, dimensionality reduction of the frequencies for variable selection is done using n the foregoing example, the total frequencies may be reduced from 512 to 18.

The data from the dimensionality regression module (0901) may be processed with a Variance inflation factors module (VIF) (0902). The VIF module measures how much the variance of the estimated regression coefficients are inflated as compared to when the predictor variables are not linearly related. The VIF is used to describe how much multicollinearity (correlation between predictors) exists in a regression analysis. As it is known, Multicollinearity is problematic because it can increase the variance of the regression coefficients, making them unstable and difficult to interpret. The square root of the variance inflation factor indicates how much larger the standard error is, compared with what it would be if that variable were uncorrelated with the other predictor variables in the model. For Example, if the variance inflation factor of a predictor variable were 5.27 ($\sqrt{5.27}=2.3$) this means that the standard error for the coefficient of that predictor variable is 2.3 times as large as it would be if that predictor variable were uncorrelated with the other predictor variables.

The data from variance inflation factors module (VIF) (0902) may further be processed with a principal component analysis module (0903). Principal component analysis (PCA) is a technique used to emphasize variation and bring out strong patterns in a dataset. It's often used to make data easy to explore and visualize. As defined in the art, Principal component analysis (PCA) is a statistical procedure that uses an orthogonal transformation to convert a set of observations of possibly correlated variables into a set of values of linearly uncorrelated variables called principal components. The number of principal components is less than or equal to the number of original variables. This transformation is defined in such a way that the first principal component has the largest possible variance (that is, accounts for as much of the variability in the data as possible), and each succeeding component in turn has the highest variance possible under the constraint that it is orthogonal to (i.e., uncorrelated with) the preceding components. According to a preferred exemplary embodiment, a principal components analysis is used to determine most relevant frequencies in the acoustic signal for developing a quantitative acoustic texture model. It should be noted that any other analysis technique known in the art may be used to identify principal components such as the relevant frequencies.

The data from the PCA module (0903) is further regressed with a best subsets regression module (0904) which is used to determine which of these most relevant frequencies are best for texture attribute model building with good correlation. An $R^2$ value greater than 0.9 may be considered a good correlation between the measure value from the model and descriptive expert panel number.

Exemplary Texture Attribute Measurement Method

As generally shown in FIG. 10, an exemplary texture measurement method may be generally described in terms of the following steps:

(1) eating/drinking a food product (1001);
  - a human being may eat a food product via a molar chew, a natural chew and/or a frontal bite. Once an eating method is selected, the eating method may be consistently utilized throughout the process of development of the acoustic in-situ model and also for capturing the acoustic signal.

(2) generating an acoustic signal from eating/drinking the food product (1002);
  - an acoustic signal may be generated during eating from a jawbone conduction that may vibrate an eardrum and change the pressure of the air surrounding the ear drum. Jawbone conduction is the conduction of sound to the inner ear through the bones of the skull. Bone conduction is one reason why a person's voice sounds different to them when it is recorded and played back. Because the skull conducts lower frequencies better than air, people perceive their own voices to be lower and fuller than others do, and a recording of one's own voice frequently sounds higher than one expects it to sound. The acoustic signals during the process of drinking or eating or chewing are perceived differently by different human beings. An in-situ measure of the acoustic signals and a model enables to distinguish various food snacks and liquids.

(3) capturing the acoustic signal with an acoustic capturing device (1003);

(4) converting the acoustic signal from a time domain to a frequency domain (1004);

(5) identifying relevant frequencies and their associated intensities (1005); and (6) quantifying said texture attribute of the food product based on the relevant frequencies and the associated intensities (1006).

The texture attribute of the food snack may be measured with an in-situ acoustic texture model. It should be noted that the in-situ acoustic texture model used to measure a texture attribute may be compensated for changes in the properties of the human saliva such as viscosity and pH. According to a preferred exemplary embodiment, the calibration model may further be developed to adjust or compensate for background noise, human to human variation and method of eating/drinking.

This general method summary may be augmented by the various elements described herein to produce a wide variety of invention embodiments consistent with this overall design description. According to a preferred exemplary embodiment, when a food or beverage item is consumed a texture attribute may be measured with the acoustic fingerprint of each food and beverage item which include the interaction with human saliva. Differentiating sweeteners at the concentrations they are found in beverages for example a Diet Pepsi® vs. a regular Pepsi® and when in contact with saliva, different sweeteners can have different interactions with human saliva given their chemical composition, the mixture of the beverage and the saliva produces viscosity differences that can be modeled with an in-situ model as described above in FIG. 10 (1000).

Exemplary Texture Attribute Correlation Method

Figure 11:
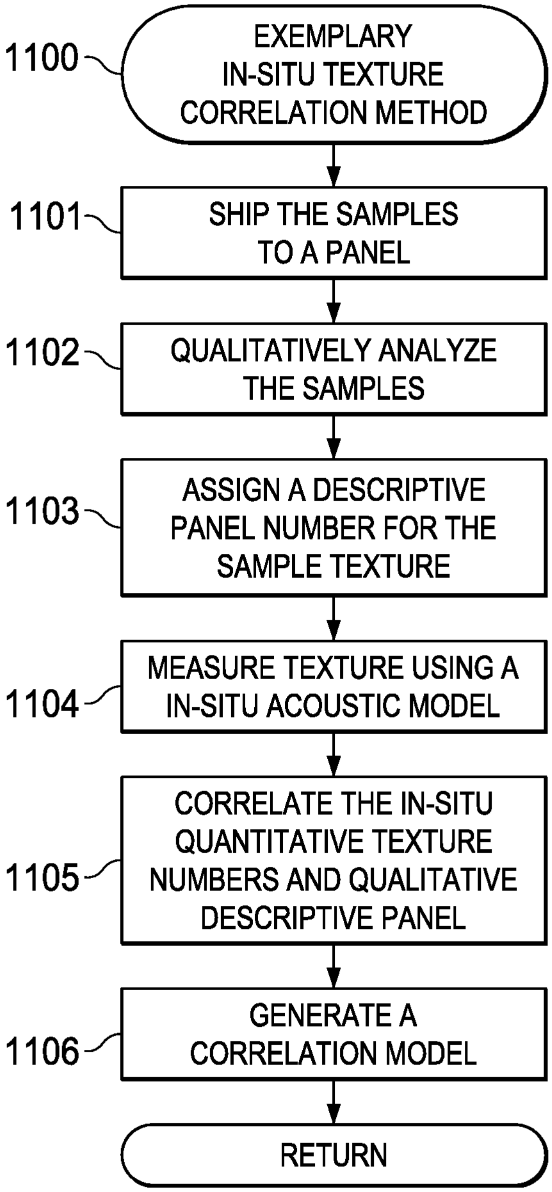
FIG. 11 is an exemplary flow chart method for quantitative correlation of texture according to a preferred embodiment of the present invention.

As generally shown in FIG. 11, an exemplary texture correlation method may be generally described in terms of the following steps:

(1) Shipping food snack samples to an expert panel (1101);

The shipping of the food snack samples may take time and the food snack may undergo texture change during the shipping process. The number of times samples are shipped to an expert panel is substantially reduced due a high correlation in-situ model developed according to a preferred exemplary embodiment.

(2) Qualitatively analyzing the food snack samples (1102);

quantitatively measure texture attributes by an expert panel for assigning taste panel scores ("descriptive panel number").

(3) Assigning a descriptive panel number for the texture attributes of the food snack sample (1103);

(4) Measuring texture attributes with an in-situ quantitative acoustic model (1104);

The in-situ model may be compensated with different coefficients to account for individual human saliva and chewing preferences. For example, Human A may be chewing with saliva having a viscosity A and pH A and use a chew pattern A. Human B may be chewing with saliva having a viscosity B and pH B and use a chew pattern B. When the in-situ model is developed using method described in FIG. 12 (1200), the coefficients may be different for Human A vs. Human B to account for the differences. A unique model may be used for each of the texture attributes. Therefore, the texture attribute would be same independent of the human eating/drinking the solid/liquid.

(5) Correlating the texture attribute as measure by the in-situ quantitative and the qualitative expert panel texture attributes (1105); and (6) Generating a correlation model for the texture attributes (1106).

This general method summary may be augmented by the various elements described herein to produce a wide variety of invention embodiments consistent with this overall design description.

Exemplary Texture Attribute Model Development Method (1200)

As generally shown in FIG. 12, an exemplary texture attribute model development method may be generally described in terms of the following steps:

(1) Receiving a raw acoustic signal (1201);

(2) Filtering, smoothing and transforming the raw acoustic signal (1202);

The signal may be adjusted for background noise. For example an empty cell may be used to capture background frequencies that may be compensated by addition or deletion in the captured acoustic signal. The background noise may be compensated for frequencies below 20 KHz and may not be compensated for frequencies above 20 KHz.

(3) Regressing and identifying relevant frequencies (1203);

(4) Generating a model for the texture attributes (1204).

Coefficients for the model may be determined based on step (1203) and adjusted or compensated for saliva properties and chewing mechanism.

This general method summary may be augmented by the various elements described herein to produce a wide variety of invention embodiments consistent with this overall design description.

It should be noted that the method used to generate the aforementioned texture attribute model may be used to generate models for other food properties such a moisture, solids content, oil content, slice thickness, density, blister density and topical seasonings. The relevant frequencies and associated intensities and the coefficients of the developed model may change depending on the food property that is measured with the acoustic method.

Exemplary Acoustic Signal Method (1300)

Figure 13:
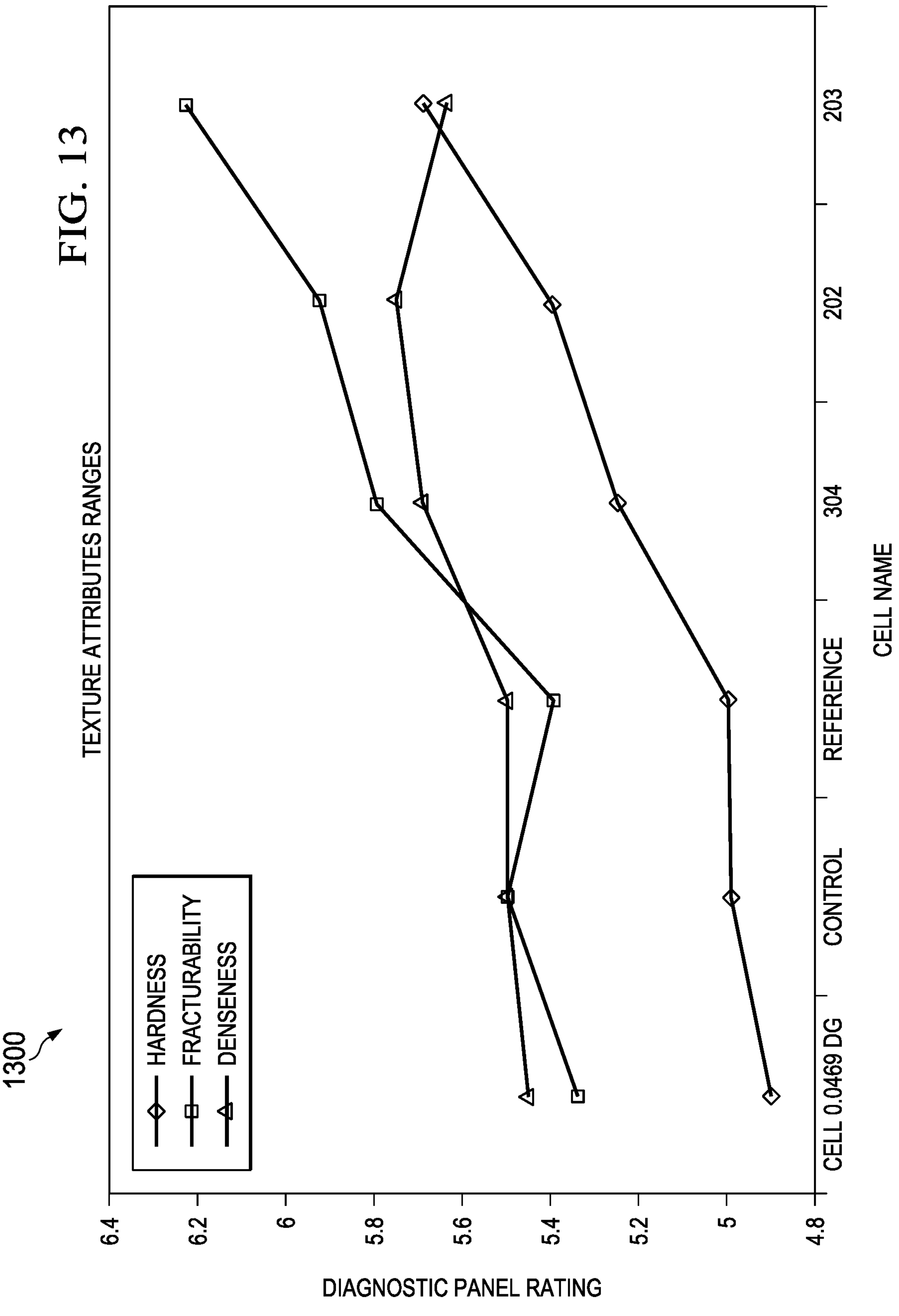
FIG. 13 an exemplary descriptive panel number versus texture attribute chart according to a preferred embodiment of the present invention.

As generally illustrated in FIG. 13, an exemplary correlation plot between quantitative acoustic texture attributes such as hardness (diamond shaped points), denseness (triangle shaped points), and fracturability (square shaped points) on x-axis and expert panel number on y-axis is shown. According to a preferred exemplary embodiment, the adjusted $R^2$ is greater than 0.9.

Exemplary Acoustic Signal Processing Method (1400)

Figure 14:
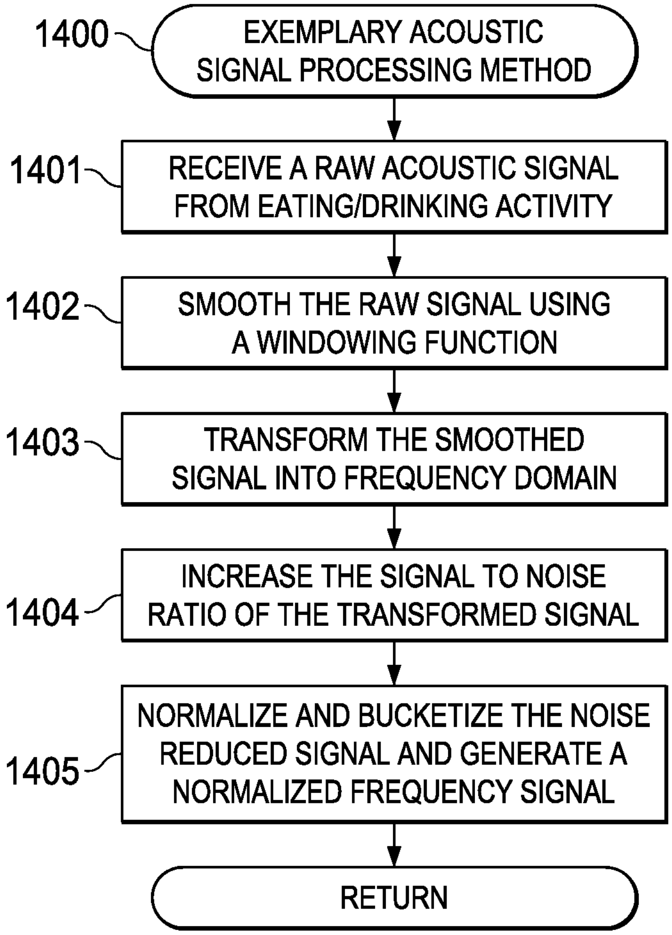
FIG. 14 is an exemplary flow chart method for acoustic signal processing according to a preferred embodiment of the present invention.

As generally shown in FIG. 14, an exemplary Acoustic Signal Processing method may be generally described in terms of the following steps:

(1) Receiving an raw acoustic signal (1401);
(2) Smoothing the raw acoustic signal with a windowing function to create a smoothened acoustic signal (1402);
(3) Transforming the smoothened acoustic signal into a frequency domain signal (1403);
(4) Increasing the signal-to-noise of the frequency domain signal (1404); and
(5) Normalizing and bucketing the frequency domain signal (1405).

This general method summary may be augmented by the various elements described herein to produce a wide variety of invention embodiments consistent with this overall design description.

Exemplary Acoustic Statistical Processing Method (1500)

Figure 15:
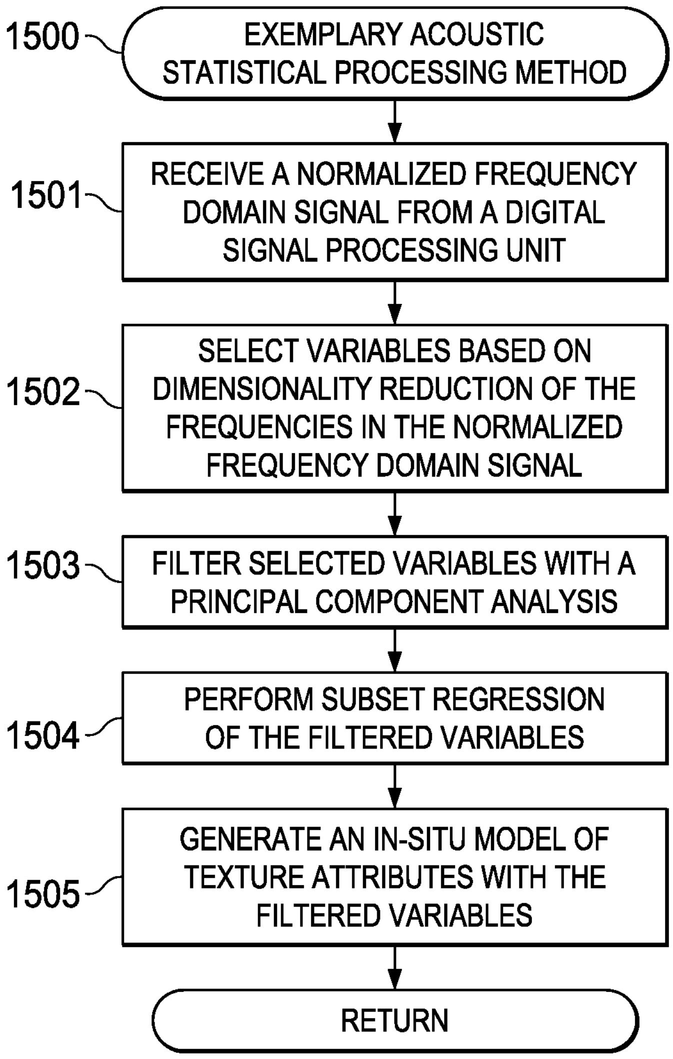
FIG. 15 is an exemplary flow chart method for acoustic statistical processing according to a preferred embodiment of the present invention.

As generally shown in FIG. 15, an exemplary Acoustic Signal Generation method may be generally described in terms of the following steps:

(1) Receiving a frequency domain acoustic signal (1501);
(2) Selecting variables based on dimensionality reduction of the frequencies in the frequency domain acoustic signal (1502);
(3) Filtering selected variables with a principal component analysis (1503);
(4) Performing subset regression of the filtered variables (1504); and
(5) Generate an in-situ model of texture attributes with the filtered variables (1505).

The filtered variables may be the relevant frequencies in the acoustic signal that show a strong correlation. This general method summary may be augmented by the various elements described herein to produce a wide variety of invention embodiments consistent with this overall design description.

Exemplary Food Snack Finger Printing Method (1600)

Figure 16:
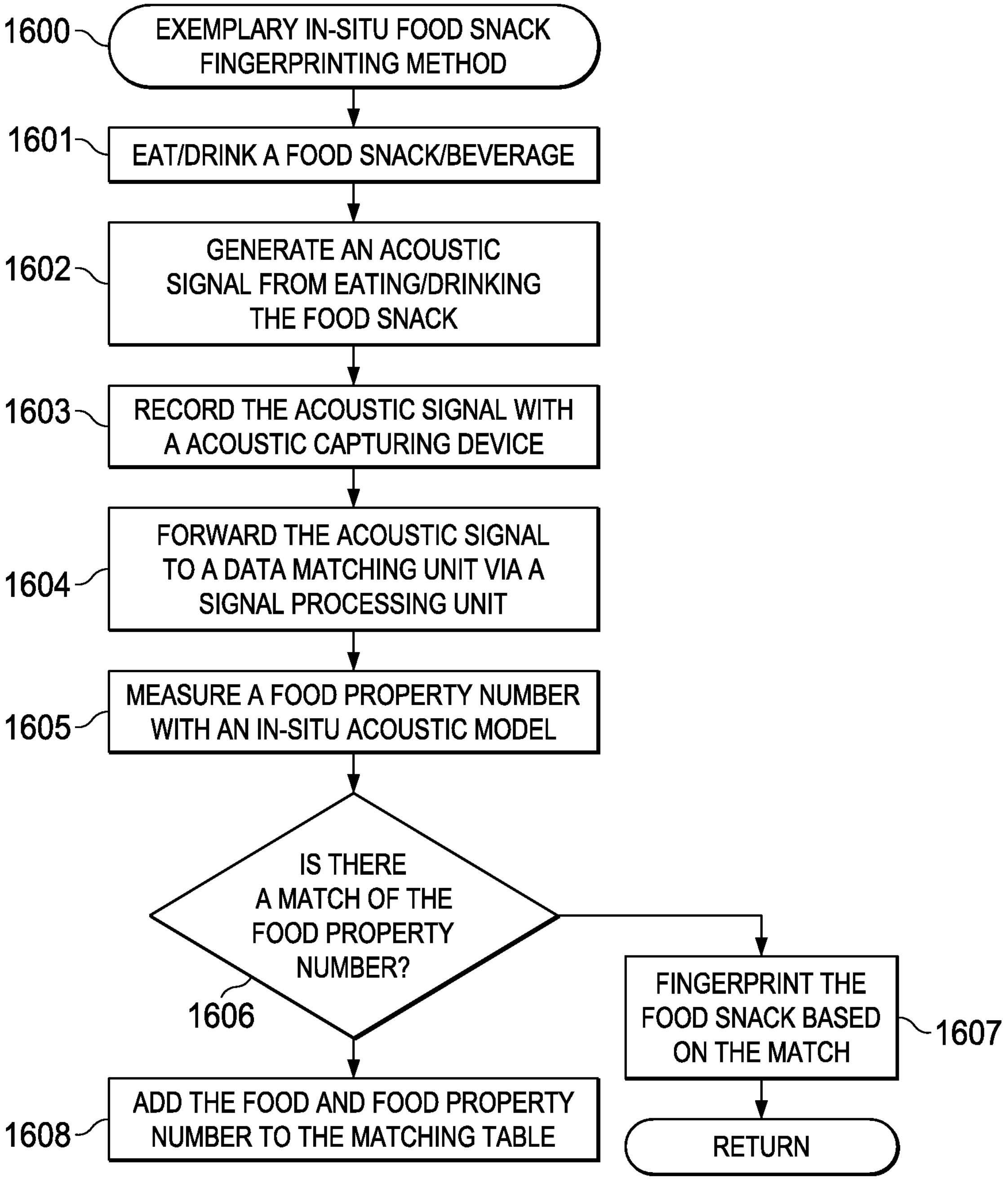
FIG. 16 is an exemplary food snack fingerprinting method according to a preferred exemplary embodiment.

As generally shown in FIG. 16, an exemplary food snack finger printing method may be generally described in terms of the following steps:

(1) eating/drinking a food snack (1601);
(2) generating an acoustic signal from eating/drinking the food snack (1602);
(3) capturing the acoustic signal with an acoustic capturing device (1603);
(4) forwarding the acoustic signal to a data matching unit (1604);
(5) measuring a food property number of the food snack with an in-situ acoustic model (1605);
(6) comparing the food property number with an entry in a matching table (1606);
(7) if a match exists in step (1606), finger printing the food snack (1607); and
(8) if a match does not exist in step (1606), adding the food snack to the database for further use (1608).

The above method enables a human being to distinguish and identify foods or beverages by a simple act of consumption and recording the acoustic signal. For example, a sweetened beverage can be distinguished from another sweetened beverage by consuming both the beverages separately and recording the acoustic signals. The acoustic signals may then be matched to a preexisting database and then identified. The exemplary method (1600) may be utilized to conduct blind taste testing and target specific responses of the taste testing. A harder food snack may generate an acoustic signal associated with frequencies and intensities that are different than a softer food snack. Similarly, a food snack with a greater oil content may generate an acoustic signal associated with frequencies and intensities that are different than a less oil content food snack. Likewise, a beverage which is acidic may generate an acoustic signal associated with frequencies and intensities that are different than a non-acidic beverage. This general method summary may be augmented by the various elements described herein to produce a wide variety of invention embodiments consistent with this overall design description.

Exemplary Food Property Matching Table (1700)

As generally illustrated in FIG. 17, an exemplary food property matching table (1700) is shown. The table may include a food snack in column (1701) and an associated food property (1702) in another column. The entries (1710, 1711) may include data for the food snack and food property for matching purposes. For example, food snack column (1701) may comprise various solids and/or liquids and their associated texture or liquid properties in column (1702). Each of the entries in the table (1700) may be populated after an in-situ model for the food snack has been developed by the aforementioned methods described in FIG. 12 (1200). For example, an entry (1711), may be a potato chip A. A range for the texture or other food properties may be determined with the in-situ acoustic model for the potato chip A and entered as an entry in table (1700). Similarly, food properties for other food products are measured with the in-situ acoustic model and entered into the table. The in-situ acoustic model may or may not be correlated with an expert panel number. The food property may be a single texture attribute, a combination of texture attributes or a composite number comprising a combination of other food properties such as moisture, brittleness, solid content and so on. When a food snack is measured with an in-situ measurement method a food property number may be determined. The food property number may be obtained from a single sample or an average of multiple samples. The measured food property number may then be looked up in the column (1702) in the matching table (1700) and a corresponding food snack is determined in the column (1701). Thereby, a food snack is finger printed based on in-situ measurement. According to an exemplary embodiment, food snacks with subtle differences in food property may be differentiated with the food finger printing technique. For examples, various potato chips such as baked, fried, and/or textured may be differentiated by measuring each of them and looking up the corresponding potato chip in the matching table (1700) from the measured food property numbers. Foods may be separated into buckets with the in-situ measurement and matching process as aforementioned in FIG. 16 (1600). Similarly, liquids with subtle differences may be put into separate buckets based on a particular liquid property such as viscosity, sweetness, mouth feel, density, pH and so on.

Exemplary Discrete in-Line Feedback Control with In-Situ Acoustic Quantitative Texture Measurement (1800)

As generally illustrated in FIG. 18 (1800), a food snack manufacturing system comprising an in-situ Acoustic Quantitative Texture Measurement apparatus (1806) is positioned after a food processing unit (FPU) (1805). The system (1800) illustrated in FIG. 18 (1800) may be used to manufacture potato chips. The manufacturing system may comprise a series of stations that include a sourcing stage (1801), a storage station (1802), wash/peel station (1803), slicing station (1804), frying station (1805), measurement station (1806), a seasoning station (1807), a packaging station (1808) and a labeling station (1809). The food snacks, such as potato chips, may be conveyed from station to station on a conveyor belt in the manufacturing system. According to a preferred exemplary embodiment, an in-line feedback control with in-situ acoustic quantitative texture measurement apparatus enables to manufacture consistent food texture quality. The acoustic quantitative texture measurement apparatus may be positioned immediately after (downstream) the FPU (1805) and before a seasoning unit (1807) or packaging unit (1808). A human being (1813) may be positioned close to the acoustic quantitative texture measurement apparatus (1806) to consume food snack output from FPU (1805). According to a preferred exemplary embodiment, the apparatus (1806) records/captures acoustic signal when the human being (1813) consumes (eats/drinks) food snack from FPU (1805) and processes the acoustic signal to quantitatively measure a texture attribute. According to a preferred exemplary embodiment, depending on the measured texture attribute, the human being may adjust process parameters in an output controller (1812) to control the output quality from the FPU (1805). The output controller (1812) may be connected to a slicing input controller (1810) and a frying input controller (1811). Typical process control equipment such as PI, PID control devices, may be used to control the input parameters of the slicing and frying units. For example, if the texture attribute, hardness falls outside an acceptable limit, a human being may program the output controller (1812) to adjust an input parameter to the frying unit such as frying temperature or frying time. The human being may also adjust program the output controller (1812) to adjust an input parameter to the slicing unit so that the slices are thinner or thicker depending on the correlation of the output texture attribute to the input parameters.

Exemplary Discrete in-Line Feedback Control with In-Situ Acoustic Quantitative Texture Measurement (1900)

A discrete feedback method for controlling a texture attribute of food product continuously output from a food processing unit, the method comprises the steps of:

(1) Processing food ingredients in said food processing unit to produce said food product (1901);

(2) Consuming the food snack at set interval (1902);

The interval may be set as short as 10 minutes to as long as 6 hours. Shorter intervals provide a tight quality control as the sample selected to measure texture is representative of the interval. According to a preferred exemplary embodiment, the interval is set within a range of 1 min to 10 hours. According to a preferred more exemplary embodiment, the interval is set to 30 minutes hour. According to a most preferred exemplary embodiment, the interval is set to 1 hour.

(3) Quantitatively measuring a texture attribute of said food product with a texture measuring tool and a correlated in-situ acoustic texture model (1903);

An apparatus as aforementioned in FIG. 5 (0500) may be used to measure a texture attribute such as hardness, fracturability, or denseness.

(4) If said texture attribute measured in step (3) is outside an acceptable limit, feeding back information to said food processing unit to adjust input parameters to said food processing unit such that a texture attribute measured for subsequent food products produced from said food processing unit falls with said acceptable range (1904);

An acceptable limit may be established for each of the texture attributes based on a taste panel correlation. The input process parameters to the food processing units such as fryer and slicing units are adjusted manually. If the measured texture attribute with the in-situ apparatus falls outside of an acceptable range, an output controller (1812) may be adjusted to control the output quality from the food processing unit. The acceptable range may be based on a correlated expert panel number or past experience with mouthfeel. This provides a significant advantage over prior method of tasting the food snack and comparing it to a reference sample. The in-situ method enables a quantitative feedback to the food processing unit, rather than a qualitative feedback as currently performed in the art.

This general method summary may be augmented by the various elements described herein to produce a wide variety of invention embodiments consistent with this overall design description.

Figure 19:
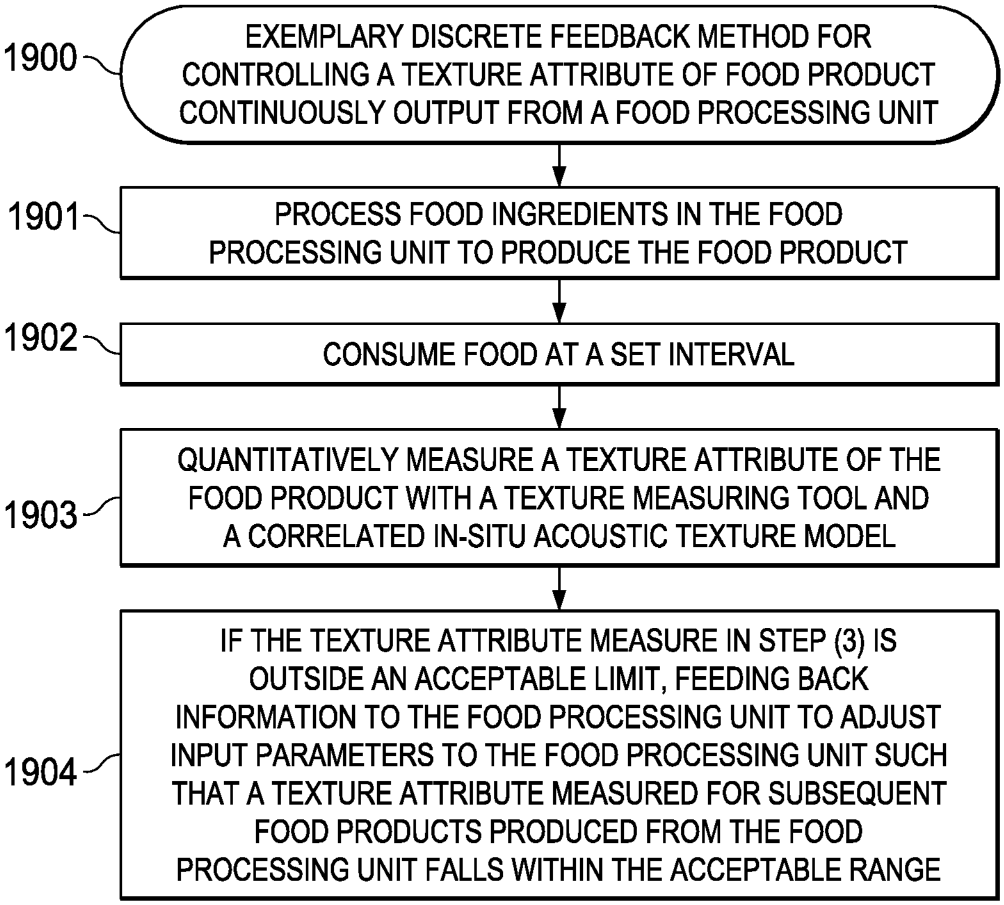
FIG. 19 is an exemplary quantitative in-situ discrete texture feedback manufacturing method according to a preferred embodiment of the present invention.

A discrete feedback system for controlling texture of a food product in a continuous manufacturing process using the method described above in FIG. 19 (1900) may comprise a food pre-processing unit, a food processing unit, a texture measuring tool positioned downstream from the food processing unit, wherein the texture measuring tool is configured to quantitatively measure a texture attribute of the food product that is output from the food processing unit when a human being eats or drinks a portion of the food product and an acoustic capturing device to capture an acoustic signal generated by the eating or drinking activity, and a controller controlling a plurality of input parameters to the food processing unit and the food pre-processing unit based on input from the texture measuring tool. According to a preferred exemplary embodiment, the controller utilizes the texture attribute information to control the plurality of input parameters to the food processing unit and the food pre-processing unit such that a texture attribute of a resultant food product output from the food processing unit falls within an acceptable limit.

According to another preferred exemplary embodiment, a discrete feedforward system for controlling texture of a food product in a continuous manufacturing process, may comprise a food pre-processing unit, a food processing unit, a texture measuring tool positioned downstream from the food pre-processing unit, wherein the texture measuring tool is configured to quantitatively measure an input attribute of food ingredients that are input to said food pre-processing unit when a human being eats or drinks a portion of the food ingredients and an acoustic capturing device to capture the acoustic signal generated by the eating activity; and a controller controlling a plurality of input parameters to the food processing unit and the food pre-processing unit based on input from the texture measuring tool. A feedforward method for controlling output texture of a food product using the aforementioned feedforward system, the method may be generally described in terms of the following steps:

(1) measuring an input texture attribute of food ingredients with an input texture measuring tool and a eating activity;

(2) programming plural input parameters to a food processing unit based on the input texture attribute;
(3) producing food product from the food processing unit; and
(4) measuring an output texture attribute of the food product with an output texture measuring tool and a eating activity.

The step of measuring the output texture attribute may further comprise the steps of:

(5) determining if the output texture attribute is within an acceptable output limit; and
(6) if the output texture attribute is outside an acceptable output limit, feeding back output texture attribute information to an output controller to adjust the input parameters to the food processing unit;

Exemplary Acoustic Signal Time Domain to Frequency Domain Conversion (2000)

Figure 20:
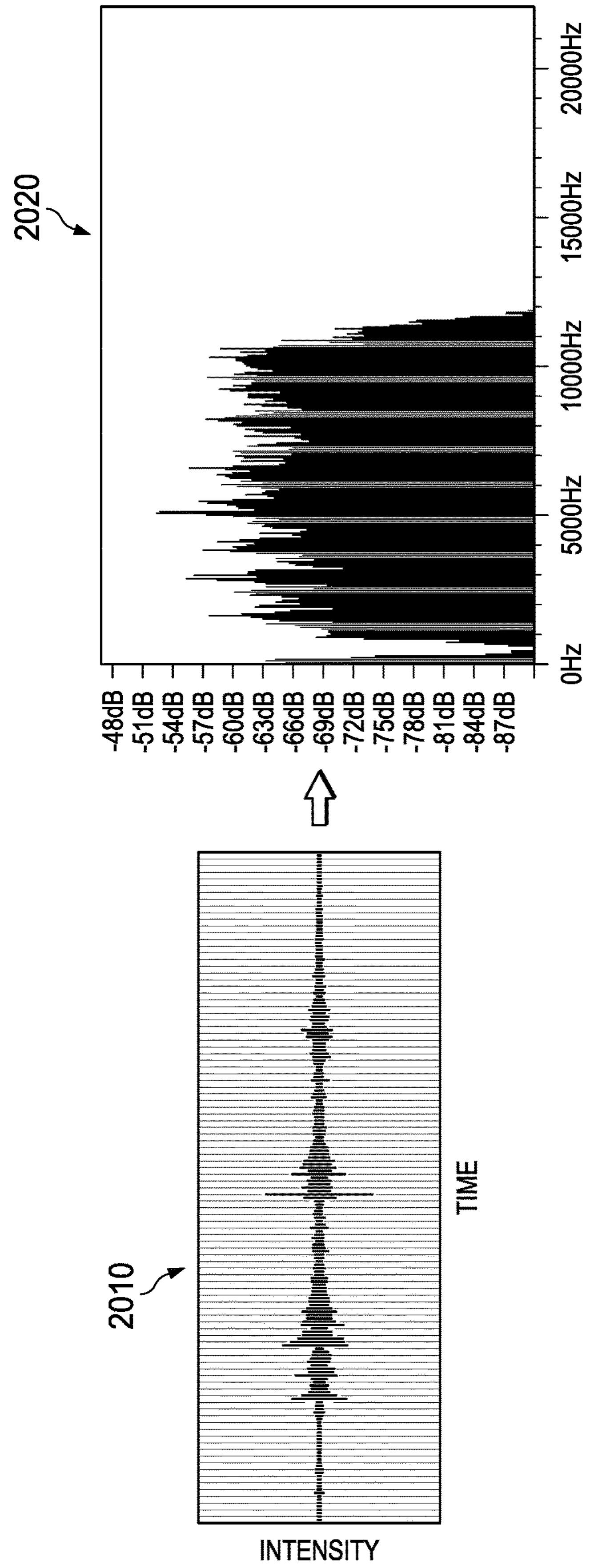
FIG. 20 is an exemplary acoustic signal time domain to frequency domain transformation chart according to a preferred embodiment of the present invention.

As generally illustrated in FIG. 20, an exemplary acoustic signal captured in time domain (transient) (2010) is converted to a frequency domain (2020) with Fourier transformation. During an eating activity of a food snack, an acoustic signal is captured in time domain and is recorded and plotted as Intensity (dB) vs. time (secs). The recorded acoustic signal may be transformed into a frequency domain signal as illustrated in FIG. 20 (2020). The transformed acoustic signal may be further processed to identify relevant frequencies based on a statistical regression analysis. An acoustic model to quantitatively measure a texture attribute may be developed with the identified relevant frequencies and their associated intensities as variables.

Exemplary Texture Attribute vs. Relevant Frequencies Chart (2100-2300)

Figure 21:
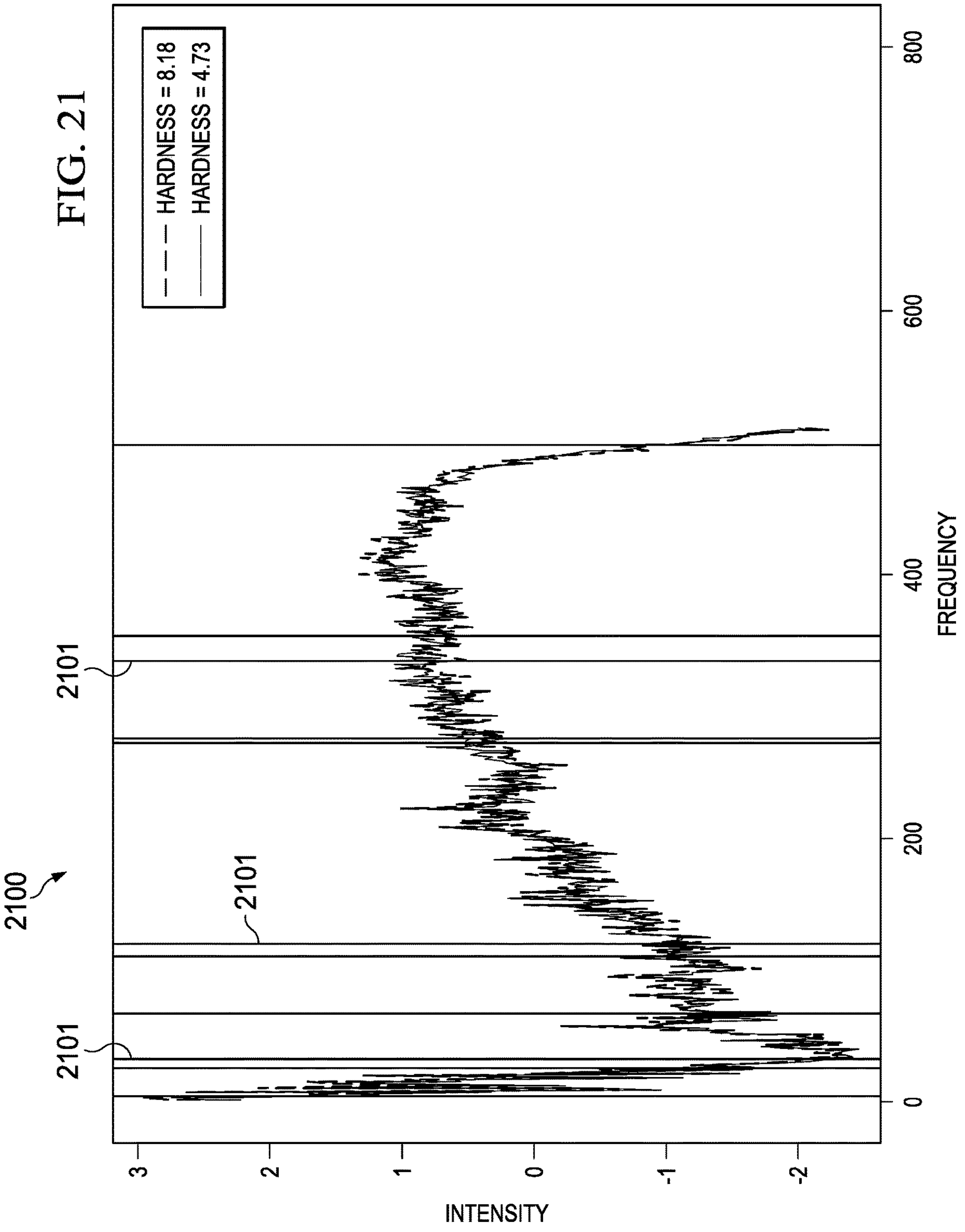
FIG. 21 is an exemplary texture attribute (hardness) vs. relevant frequencies chart according to a preferred embodiment of the present invention.
Figure 22:
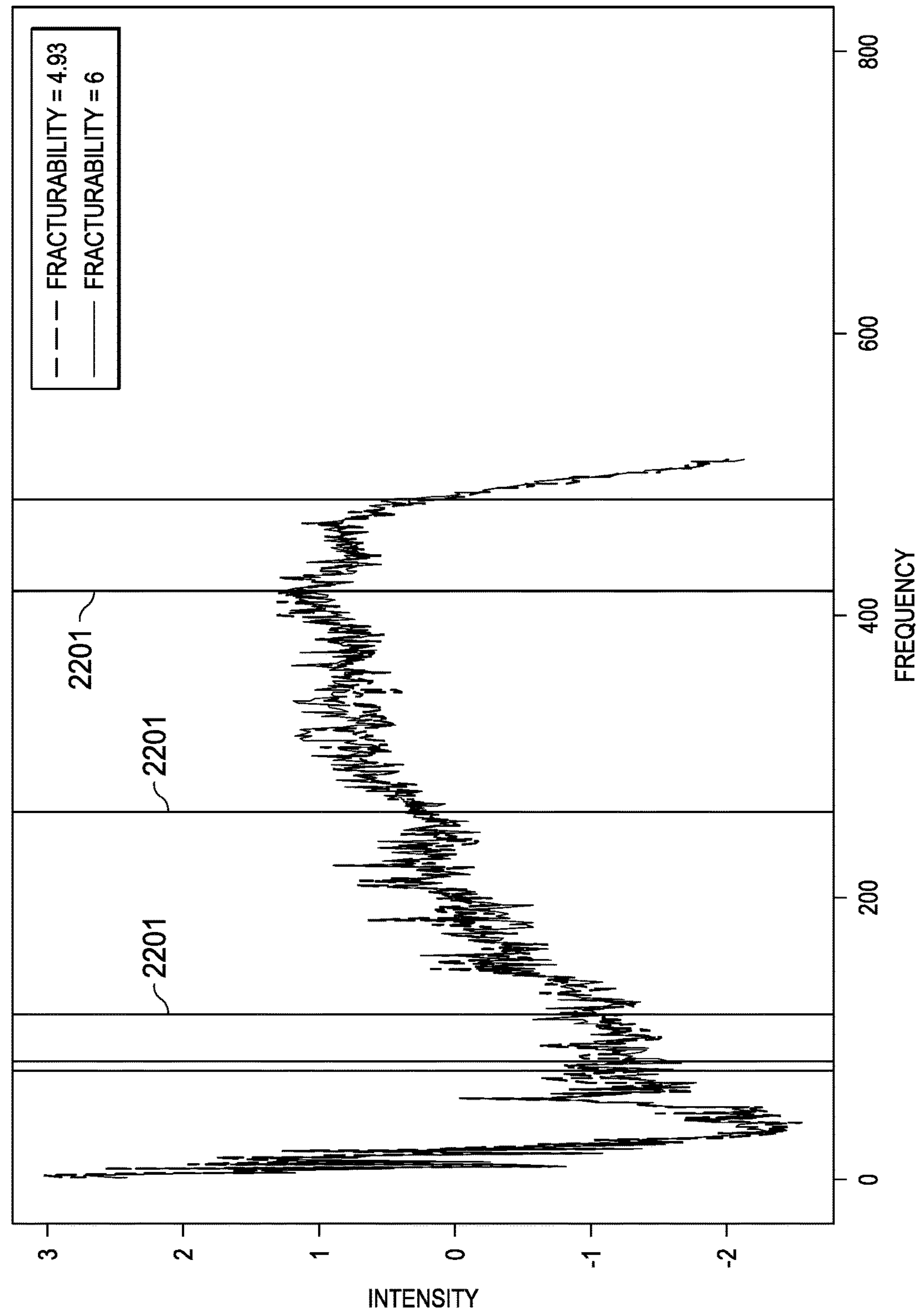
FIG. 22 is an exemplary texture attribute (fracturability) vs. relevant frequencies chart according to a preferred embodiment of the present invention.

As generally illustrated in FIG. 21 and FIG. 22, an exemplary texture attribute vs. relevant frequencies chart may be used to compute the hardness of a food snack. The relevant frequencies may be identified by a statistical regression for a particular texture attribute and a food snack. For example, frequencies (2101) may be relevant for hardness and frequencies (2201) may be relevant for fracturability. According to a preferred exemplary embodiment, the relevant frequencies and corresponding intensities identified in a transformed acoustic signal may be substituted in an acoustic model to quantitatively measure a texture attribute such as hardness. It should be noted that the frequencies indicated on x-axis are frequency "buckets" as determined by an algorithm, and not the literal frequencies (i.e. 400 is not 400 Hz, it is more like 18,000 Hz).

Figure 23:
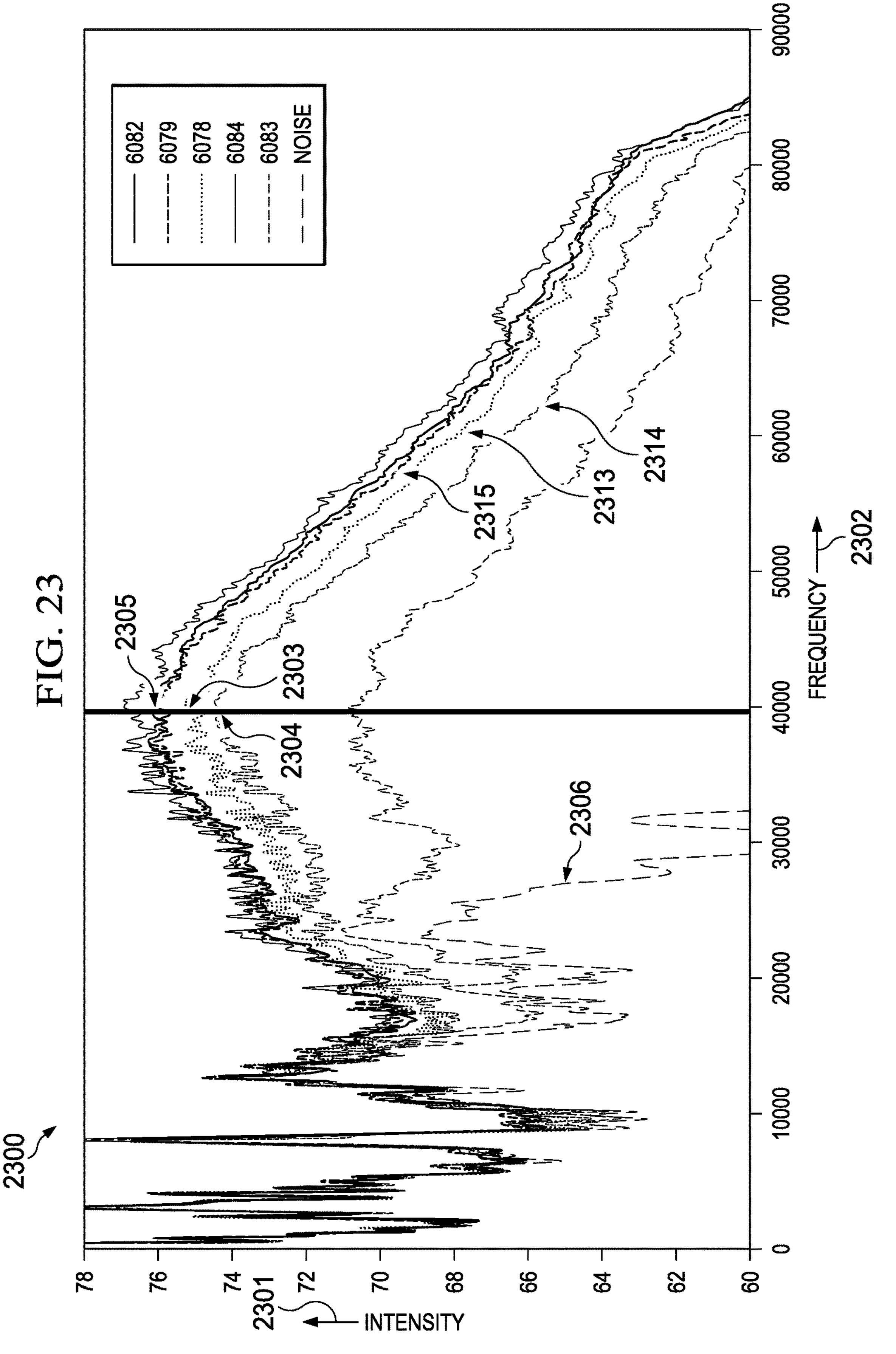
FIG. 23 is another exemplary texture attribute (hardness) vs. relevant frequencies chart according to a preferred embodiment of the present invention.

As generally illustrated in FIG. 23, an exemplary texture attribute Intensity (dB) (2301) vs. relevant frequencies (2302) chart for a food snack treated with various input conditions. Plot (2314), (2315), (2316) are frequency vs. Intensity graphs for a potato chip with different solid content, moisture content and hardness of the input ingredients such as potatoes. For example, a plot (2314) may be a frequency vs. intensity plot for a food snack that has a different solids content in the input ingredients. Similarly, a plot (2315) may be a frequency vs. intensity plot for a food snack that has a different moisture content and different hardness in the input ingredients respectively. A plot (2306) may be plotted for background noise so that the resulting plot may be compensated for the noise. After identifying the relevant frequencies for a food snack such as a potato chip, an acoustic signal may be captured for each of the input conditions and the acoustic signal may be further processed to determine the intensities associated with the identified frequencies for the food property of the food snack. For example in FIG. 23, an identified frequency 40000 Hz may have an intensity of 75 dB (2303) for plot (2313), an intensity of 74 dB (2304) for plot (2314) and an intensity of 76 dB (2305) for plot (2315). The intensities may be substituted into a food property model generated by aforementioned equation (2) and a food property such as a texture attribute may be calculated. As illustrated in FIG. 23, the 3 different input conditions of the food ingredients (solids content, moisture content and hardness) resulted in 3 different associated intensities which further result in 3 different texture attributes. Therefore, an acoustic signal may be captured and processed for a food product and a texture attribute may be calculated based on the relevant frequencies. The input conditions may be tailored to achieve a desirable texture attribute value that is within a predefined limit. The predefined limit may be correlated to a qualitative descriptive panel number. Similarly, plots may be generated for various food properties by capturing an acoustic signal and processing it. The intensities associated with the various food properties at their respective frequencies may be determined and the food property may be calculated. A model may be generated for each of the food properties through signal processing and statistical regression as aforementioned. Therefore, an in-situ method may be used to identify differences in a food product based on any food property such as a texture attribute, moisture, oil content, density, viscosity or mouthfeel. The differences in the food product may be as minor as +−5% of the desirable value. For example, a desirable hardness value of 75 may provide an acoustic signature that may be differentiated from a hardness value of 70 that may be undesirable for the food product. The food product with the undesirable value (70) may be rejected and not further processed or packaged.

System Summary

The present invention system anticipates a wide variety of variations in the basic theme of in-situ texture measurement with an apparatus that includes an acoustic capturing device and a data processing unit. When a human being eats/drinks a food snack, the physical interaction in the mouth sends pressure waves that propagate through the ear bone and produce an acoustic signal. The acoustic capturing device records and forwards the signal to a data processing unit. The data processing unit further comprises a digital signal processing module that smoothens, transforms and filters the received acoustic signal. A statistical processing module further filters the acoustic signal from the data processing unit and generates a quantitative acoustic model for texture attributes such as hardness and fracturability. The quantitative model is correlated with a qualitative texture measurement from a descriptive expert panel. Another method includes a food snack fingerprinting using an in-situ quantitative food property measurement.

This general system summary may be augmented by the various elements described herein to produce a wide variety of invention embodiments consistent with this overall design description.

Method Summary

The present invention method anticipates a wide variety of variations in the basic theme of implementation, but can be generalized as a method of quantitatively measuring texture of a food snack, the method comprises the steps of:

(1) eating/drinking a food snack;
(2) generating an acoustic signal from eating/drinking the food snack;
(3) capturing the acoustic signal with an acoustic capturing device;
(4) converting the acoustic signal from a time domain to a frequency domain;
(5) identifying relevant frequencies and their associated intensities; and
(6) quantifying said texture attribute of the food product based on the relevant frequencies and the associated intensities.

This general method summary may be augmented by the various elements described herein to produce a wide variety of invention embodiments consistent with this overall design description.

System/Method Variations

The present invention anticipates a wide variety of variations in the basic theme of in-situ quantitative texture attribute measurement. The examples presented previously do not represent the entire scope of possible usages. They are meant to cite a few of the almost limitless possibilities.

This basic system and method may be augmented with a variety of ancillary embodiments, including but not limited to:

- An embodiment wherein the data processing unit further comprises a digital signal processing unit and a texture attribute calculation unit.
- An embodiment wherein the digital signal processing unit is configured to smoothen, transform and filter the acoustic signal to identify relevant frequencies relating to the texture attribute.
- An embodiment wherein the texture attribute calculation unit is configured to calculate the texture attribute from the relevant frequencies.
- An embodiment wherein the texture attribute is selected from a group comprising: hardness, fracturablity, and denseness.
- An embodiment wherein the eating activity is a frontal bite with tooth of the human being.
- An embodiment wherein the eating activity is a molar chew of the human being.
- An embodiment wherein the eating activity is a natural chew of the human being.
- An embodiment wherein the food snack is a solid.
- An embodiment wherein the food snack is a liquid.
- An embodiment wherein the acoustic capturing device is a microphone; the microphone is configured to be wired to the data processing unit.
- An embodiment wherein the acoustic capturing device is a microphone; the microphone is configured to wirelessly connect with the data processing unit.
- An embodiment wherein the acoustic capturing device is configured to capture acoustic waves within the frequency range.
- An embodiment wherein the acoustic capturing device is configured to capture sound waves in a single direction.
- An embodiment wherein the acoustic capturing device is configured to capture sound waves in all directions.
- An embodiment wherein the acoustic capturing device is integrated with the digital signal processing unit.

One skilled in the art will recognize that other embodiments are possible based on combinations of elements taught within the above invention description.

Discrete In-Situ Feedback Manufacturing System Summary

The present invention system anticipates a wide variety of variations in the basic theme of a discrete feedback system for controlling texture of a food snack in a manufacturing process. The system comprises an in-situ texture measuring tool positioned downstream of a food processing unit along with a human being consume a food snack from the food processing unit at a set interval. The in-situ tool quantitatively measures a texture attribute of the food snack when the human being consumes the food snack. When the texture attribute is outside of an acceptable limit, the human being controls input parameters to the food processing unit such that a subsequent texture attribute of a food snack output from the food processing unit falls within the acceptable limit.

This general system summary may be augmented by the various elements described herein to produce a wide variety of invention embodiments consistent with this overall design description.

Discrete In-Situ Feedback Manufacturing Method Summary

The present invention method anticipates a wide variety of variations in the basic theme of implementation, but can be generalized as a method of quantitatively measuring texture of a food snack, the method comprises the steps of:

(1) processing food ingredients in the food processing unit to produce the food product;
(2) consuming the food product at a set interval;
(3) measuring a texture attribute of the food product with a texture measuring tool and a correlated in-situ acoustic texture model; and
(4) if the texture attribute measured in step (3) is outside an acceptable limit, feeding back information to the food processing unit to adjust input parameters to the food processing unit such that a texture attribute measured for subsequent food products produced from the food processing unit falls with the acceptable range.

This general method summary may be augmented by the various elements described herein to produce a wide variety of invention embodiments consistent with this overall design description.

What is claimed is:

1. A system for quantitative texture attribute measurement of a food snack, comprising an acoustic capturing device configured to detect an acoustic signal generated from an eating activity and in communication with a data processing unit that includes a digital signal processing unit and a texture attribute calculation unit, wherein the data processing unit is configured to:

a. smooth, transform and filter the acoustic signal,
b. identify, for a plurality of texture attributes, separate, non-overlapping relevant frequency ranges that relate to a specific texture attribute, and
c. quantitatively measure, for the plurality of texture attributes, the specific texture attribute of the food snack based on input from the acoustic capturing device and on the identification of the separate, non-overlapping relevant frequency ranges associated with the specific texture attribute.

2. The system of claim 1, wherein the specific texture attribute is selected from a group comprising: hardness, fracturability, tooth-pack, crispiness, denseness, roughness of mass, moistness of mass, residual greasiness, surface roughness, or surface oiliness.

3. The system of claim 1, wherein said eating activity is a frontal bite with tooth of said human being.

4. The system of claim 1, wherein said eating activity is a molar chew of said human being.

5. The system of claim 1, wherein said eating activity is a natural chew of said human being.

6. The system of claim 1, wherein said food snack is a solid.

7. The system of claim 1, wherein said food snack is a liquid.

8. The system of claim 1 wherein said acoustic capturing device is a microphone; said microphone is configured to be wired to said data processing unit.

9. The system of claim 1 wherein said acoustic capturing device is a microphone; said microphone is configured to wirelessly connect with said data processing unit.

10. The system of claim 1 wherein said acoustic capturing device is configured to capture acoustic waves within the frequency range of 0 to 5000 kHz.

11. The system of claim 1 wherein said acoustic capturing device is configured to capture sound waves in a single direction.

12. The system of claim 1 wherein said acoustic capturing device is configured to capture sound waves in all directions.

13. The system of claim 1, said acoustic capturing device is integrated with said digital signal processing unit.

14. The system of claim 1, said acoustic capturing device and said data processing unit are integrated into one unit.

* * * * *